US010622095B2

(12) United States Patent
Lu et al.

(10) Patent No.: US 10,622,095 B2
(45) Date of Patent: Apr. 14, 2020

(54) GENOMIC SERVICES PLATFORM SUPPORTING MULTIPLE APPLICATION PROVIDERS

(71) Applicant: Helix OpCo, LLC, San Carlos, CA (US)

(72) Inventors: James Lu, Redwood City, CA (US); Jim Chou, San Francisco, CA (US); William Lee, Mountain View, CA (US); Chris Williams, San Francisco, CA (US); James Warren, Redwood City, CA (US); Ruomu Jiang, Menlo Park, CA (US)

(73) Assignee: Helix OpCo, LLC, San Carlos, CA (US)

( * ) Notice: Subject to any disclaimer, the term of this patent is extended or adjusted under 35 U.S.C. 154(b) by 5 days.

(21) Appl. No.: 15/872,655

(22) Filed: Jan. 16, 2018

(65) Prior Publication Data

US 2019/0026428 A1     Jan. 24, 2019

Related U.S. Application Data

(60) Provisional application No. 62/535,781, filed on Jul. 21, 2017.

(51) Int. Cl.
*G06F 16/9535* (2019.01)
*G06F 16/951* (2019.01)
(Continued)

(52) U.S. Cl.
CPC ............. *G16B 30/00* (2019.02); *G06F 9/547* (2013.01); *G06F 16/951* (2019.01);
(Continued)

(58) Field of Classification Search
CPC ......... G06F 17/30864; G06F 17/30867; G06F 19/22; G06F 19/24; G06F 19/28; G06F 9/547; G06Q 30/0601; H04L 67/10
(Continued)

(56) References Cited

U.S. PATENT DOCUMENTS 9,940,266 B2    4/2018  Van Rooyen et al.
10,296,842 B2   5/2019  Lu et al.
(Continued)

FOREIGN PATENT DOCUMENTS

WO    WO-2019018262 A1    1/2019
WO    WO-2019018263 A1    1/2019
WO    WO-2019018269 A1    1/2019

OTHER PUBLICATIONS

Bumgardner et al, "Constellation: A Secure Self-Optimizing Framework for Genomic Processing", 2016 IEEE 18th International Conference on e-Health Networking, Applications and Services (Healthcom), Sep. 14-16, 2016, pp. 1-6 (Year: 2016).*
(Continued)

*Primary Examiner* — Alex Gofman
*Assistant Examiner* — Kamal K Dewan
(74) *Attorney, Agent, or Firm* — Schwegman Lundberg & Woessner, P.A.

(57) ABSTRACT

Systems, platforms, methods and media for providing genomic services are disclosed. In one example, a genomic services platform comprises a network interface through which are received genomic sequence reads derived from a biological sample obtained from a user The platform also includes a bioinformatics processing pipeline including a read alignment module configured to generate observed sequence data by aligning the sequence reads relative to a reference sequence, a variant calling module operative to identify observed variants in the observed sequence data,
(Continued)

and a variant refinement module for producing a set of refined variants associated with the user. A variant imputation module produces a set of imputed variants associated with the user, and a variant storage module disposed to receive a query from network infrastructure of a partner application provider and to provide selected ones of the refined or imputed variants in response to the query.

20 Claims, 22 Drawing Sheets

Specification includes a Sequence Listing.

(51) Int. Cl.
| | |
|---|---|
| *G16B 30/00* | (2019.01) |
| *G16B 40/00* | (2019.01) |
| *G16B 50/00* | (2019.01) |
| *G16B 50/30* | (2019.01) |
| *G16B 30/10* | (2019.01) |
| *G16B 20/20* | (2019.01) |
| *G06F 9/54* | (2006.01) |
| *G06Q 30/06* | (2012.01) |
| *H04L 29/08* | (2006.01) |

(52) U.S. Cl.
CPC ......... *G06F 16/9535* (2019.01); *G16B 20/20* (2019.02); *G16B 30/10* (2019.02); *G16B 40/00* (2019.02); *G16B 50/00* (2019.02); *G16B 50/30* (2019.02); *G06Q 30/0601* (2013.01); *H04L 67/10* (2013.01)

(58) Field of Classification Search
USPC ........................................................ 707/769
See application file for complete search history.

(56) References Cited

U.S. PATENT DOCUMENTS

| | | | | |
|---|---|---|---|---|
| 2008/0163824 | A1* | 7/2008 | Moser ..................... | G06F 19/18 119/174 |
| 2013/0096943 | A1* | 4/2013 | Carey .................... | G06Q 10/10 705/2 |
| 2014/0162257 | A1* | 6/2014 | George ............ | G01N 35/00603 435/6.11 |
| 2014/0170660 | A1* | 6/2014 | Guo ........................ | G06F 19/18 435/6.11 |
| 2015/0154646 | A1* | 6/2015 | Mishra ................... | G06Q 50/24 705/3 |
| 2015/0227697 | A1* | 8/2015 | Nelson ............... | G06Q 30/0269 705/3 |
| 2015/0331909 | A1* | 11/2015 | Sundquist ........... | G06F 16/2455 707/722 |
| 2016/0070881 | A1* | 3/2016 | Millican, III .......... | G16H 10/60 705/3 |
| 2016/0072800 | A1* | 3/2016 | Soon-Shiong ...... | H04L 63/0861 726/7 |
| 2016/0085909 | A1* | 3/2016 | Reese ................... | C12Q 1/6883 702/19 |
| 2016/0300014 | A1* | 10/2016 | Kvitek .................... | G06F 19/22 |
| 2017/0107576 | A1* | 4/2017 | Babiarz ................. | G16B 40/00 |
| 2017/0242957 | A1* | 8/2017 | Han ........................ | G06F 19/24 |
| 2017/0268051 | A1* | 9/2017 | Koehler ............... | C12Q 1/6858 |
| 2017/0308644 | A1* | 10/2017 | van Rooyen .......... | G06F 19/22 |
| 2018/0051329 | A1* | 2/2018 | Elzinga ................ | C12Q 1/6869 |
| 2019/0024161 | A1 | 1/2019 | Lu et al. | |
| 2019/0026156 | A1 | 1/2019 | Lu et al. | |
| 2019/0026429 | A1 | 1/2019 | Lu et al. | |
| 2019/0026432 | A1 | 1/2019 | Lu et al. | |
| 2019/0026433 | A1 | 1/2019 | Lu et al. | |
| 2019/0026641 | A1 | 1/2019 | Lu et al. | |
| 2019/0206512 | A1 | 7/2019 | Lu et al. | |

OTHER PUBLICATIONS

"U.S. Appl. No. 15/872,731, Preliminary Amendment filed Jul. 9, 2018", 7 pgs.
"U.S. Appl. No. 15/853,594, Non Final Office Action dated Jul. 27, 2018", 22 pgs.
"U.S. Appl. No. 15/872,731, Non Final Office Action dated Aug. 10, 2018", 21 pgs.
"International Application Serial No. PCT/US2018/042235, International Search Report dated Aug. 24, 2018", 4 pgs.
"International Application Serial No. PCT/US2018/042235, Written Opinion dated Aug. 24, 2018", 11 pgs.
"International Application Serial No. PCT/US2018/042239, International Search Report dated Aug. 28, 2018", 4 pgs.
"International Application Serial No. PCT/US2018/042239, Written Opinion dated Aug. 28, 2018", 5 pgs.
"International Application Serial No. PCT/US2018/042252, International Search Report dated Aug. 23, 2018", 4 pgs.
"International Application Serial No. PCT/US2018/042252, Written Opinion dated Aug. 23, 2018", 4 pgs.
Gottesman, et al., "The Electronic Medical Records and Genomics (eMERGE) Network", past, present, and future Genetics in Medicine vol. 15, (Oct. 2013), 761-771.
Hirschhorn, et al., "Genome-Wide Association Studies for Common Diseases and Complex", Traits Nature Reviews Genetics vol. 6, (Feb. 2005), 95-108.
Howie, "Fast and accurate genotype imputation in genome-wide association studies through pre-phasing", Nature Genetics. 44(8), (Jul. 22, 2012), 955-959.
Shendure, et al., "Next-generation DNA sequencing Nature Biotechnology", Nature Biotechnology, vol. 26, No. 10, (Oct. 2008), 1135-1145.
"U.S. Appl. No. 15/853,594, Examiner Interview Summary dated Oct. 29, 2018", 2 pgs.
"U.S. Appl. No. 15/853,594, Final Office Action dated Dec. 14, 2018", 19 pgs.
"U.S. Appl. No. 15/853,594, Response filed Oct. 26, 2018 to Non-final Office Action dated Jul. 27, 2018", 33 pgs.
"U.S. Appl. No. 15/872,731, Examiner Interview Summary dated Nov. 5, 2018", 4 pgs.
"U.S. Appl. No. 15/872,731, Notice of Allowability dated Apr. 17, 2019", 2 pgs.
"U.S. Appl. No. 15/872,731, Notice of Allowance dated Feb. 20, 2019", 9 pgs.
"U.S. Appl. No. 15/872,731, Response filed Nov. 9, 2018 to Non Final Office action dated Aug. 10, 2018", 34 pgs.
Browning, Brian, "A One-Penny Imputed Genome from Next-Generation reference Panels", The American Journal of Human Genetics, vol. 103, Issue 3, pp. 338-348, [https://www.cell.com/ajhg/fulltext/S0002-9297(18)30242-8 >, (Sep. 6, 2018), 15 pgs.
Browning, Brian, "Beagle 4.0, Version r1399", [Online]. Retrieved from the Internet: <URL: https://faculty.washington.edu/browning/beagle/b4_0.html>, (Accessed Oct. 18, 2018), 3 pgs.
Browning, Brian, "Beagle 5.0", [Online]. Retrieved from the Internet: <URL: http://faculty.washington.edu/browning/beagle/beagle.html>, (Sep. 28, 2018), 3 pgs.
Browning, S R, et al., "Rapid and Accurate Haplotype Phasing and Missing-Data Inference for Whole-Genome Association Studies by Use of Localized Haplotype Clustering", Am J Hum Genet, vol. 81, Issue 5, [Online]. Retrieved from the Internet: <URL: https://www.cell.com/ajhg/fulltext/S0002-9297(07)63882-8>, (2007), 1084-1097.
"International Application Serial No. PCT/US2018/042239, International Preliminary Report on Patentability dated Aug. 12, 2019", 8 pgs.
"International Application Serial No. PCT/US2018/042239, Response to Written Opinion filed May 21, 2019", 4 pgs.
U.S. Appl. No. 15/853,594, filed Dec. 22, 2017, Genomic Services Platform Supporting Multiple Application Providers.
U.S. Appl. No. 15/853,607, filed Dec. 22, 2017, Genomic Services Platform Supporting Multiple Application Providers.
U.S. Appl. No. 15/853,615, filed Dec. 22, 2017, Genomic Services Platform Supporting Multiple Application Providers.

(56) References Cited

OTHER PUBLICATIONS

U.S. Appl. No. 15/872,731, filed Jan. 16, 2018, Genomic Services Platform Supporting Multiple Application Providers.
U.S. Appl. No. 15/872,756, filed Jan. 16, 2018, Genomic Services Platform Supporting Multiple Application Providers.
U.S. Appl. No. 15/872,784, filed Jan. 16, 2018, Genomic Services Platform Supporting Multiple Application Providers.
U.S. Appl. No. 15/872,793, filed Jan. 16, 2018, Genomic Services Platform Supporting Multiple Application Providers.

* cited by examiner

| | | | | | | | | | | | | | | |
|---|---|---|---|---|---|---|---|---|---|---|---|---|---|---|
| 1 | ? | ? | ? | 1 | ? | 1 | ? | 0 | 2 | 2 | ? | ? | 2 | ? | 0 |
| 0 | ? | ? | ? | 2 | ? | 2 | ? | 0 | 2 | 2 | ? | ? | 2 | ? | 0 |
| 1 | ? | ? | ? | 2 | ? | 2 | ? | 0 | 2 | 1 | ? | ? | 2 | ? | 0 |
| 1 | ? | ? | ? | 2 | ? | 1 | ? | 1 | 2 | 2 | ? | ? | 2 | ? | 0 |
| 2 | ? | ? | ? | 2 | ? | 2 | ? | 1 | 2 | 1 | ? | ? | 2 | ? | 0 |
| 1 | ? | ? | ? | 1 | ? | 1 | ? | 1 | 2 | 2 | ? | ? | 2 | ? | 0 |
| 1 | ? | ? | ? | 2 | ? | 2 | ? | 0 | 2 | 1 | ? | ? | 2 | ? | 1 |
| 2 | ? | ? | ? | 1 | ? | 1 | ? | 1 | 2 | 1 | ? | ? | 2 | ? | 1 |
| 1 | ? | ? | ? | 0 | ? | 0 | ? | 2 | 2 | 2 | ? | ? | 2 | ? | 0 |

GENOTYPE DATA WITH MISSING DATA AT
UNTYPED SNPs (GREY QUESTION MARKS)

*Fig. 8A*

EACH SAMPLE IS PHASED AND THE
HAPLOTYPES ARE MODELLED AS A MOSAIC OF
THOSE IN THE HAPLOTYPE REFERENCE PANEL

REFERENCE SET OF HAPLOTYPES,
FOR EXAMPLE, HAPMAP

FROM
FIG. 8B →

FROM
FIG. 8B →

FROM
FIG. 8B →

| 1 | 1 | 1 | 1 | 1 | 0 | 1 | 0 | 0 | 2 | 2 | 0 | 2 | 2 | 0 |
| 0 | 0 | 1 | 0 | 2 | 2 | 2 | 0 | 0 | 2 | 2 | 2 | 2 | 2 | 0 |
| 1 | 1 | 1 | 1 | 2 | 2 | 2 | 0 | 0 | 2 | 1 | 1 | 2 | 2 | 0 |
| 1 | 1 | 2 | 0 | 2 | 2 | 1 | 0 | 1 | 2 | 2 | 1 | 2 | 2 | 0 |
| 2 | 2 | 2 | 2 | 2 | 1 | 2 | 0 | 1 | 2 | 1 | 1 | 2 | 2 | 0 |
| 1 | 1 | 1 | 0 | 1 | 2 | 1 | 0 | 1 | 2 | 2 | 1 | 2 | 2 | 0 |
| 1 | 1 | 1 | 2 | 1 | 2 | 0 | 0 | 2 | 1 | 1 | 2 | 1 | 1 |
| 2 | 2 | 2 | 1 | 1 | 1 | 0 | 1 | 2 | 1 | 0 | 1 | 2 | 1 | 1 |
| 1 | 1 | 1 | 0 | 0 | 2 | 0 | 0 | 2 | 2 | 2 | 1 | 2 | 2 | 0 |

THE REFERENCE HAPLOTYPES ARE USED TO
IMPUTE ALLELES INTO THE SAMPLES TO
CREATE IMPUTED GENOTYPES (SHADED)

*Fig. 8D*

| APPID | USERID | PARTNERAPPCUSTOMERID (PAC_ID) | CREATEDAT |
|---|---|---|---|
| AP-0W690YXS0GWX04AP0CR6LRN2 | US-09NU-RQ7YM | PC-222N9M5QRCXM5II8CY3U0YU | 5/31/2017 18:47 |
| AP-74NSX48N32E7N80NFX884530 | US-G1CE-S94DU | PC-2222T5F31R529BR6RJKLP24K | 6/20/2017 1:37 |
| AP-W3Q0LWH6OF9FUWNBB029ACED | US-2RZV-6SGHU | PC-222K1S3P7SROMD1WT1J39XU | 7/14/2017 17:50 |
| AP-12FZCW5G520APCG639EN38ID | US-JWV-170MV | PC-2226I13KHJ7HL77EDZAJIF8B | 5/8/2017 17:06 |
| AP-FRBEM5KAF0FMJS75TAG6SRJW | US-3GFF-9A29T | PC-222PK1X7FNTVUV1NWK5UNRXJ | 6/19/2017 17:46 |
| AP-0W690YXS0GWX04AP0CR6LRN2 | US-P3KR-XXSGM | PC-222NQXB7440NRJYRYT35L74 | 7/21/2017 15:56 |
| AP-0W690YXS0GWX04AP0CR6LRN2 | US-AF03-EZ25A | PC-222KX0TL0CRXF4NWXJ06LI5T | 5/27/2017 0:42 |
| AP-W3Q0LWH6OF9FUWNBB029ACED | US-OD5R-RHYJI | PC-222G45KPEDB04FBPIJCMNQAO | 4/21/2017 22:06 |
| AP-12FZCW5G520APCG639EN38ID | US-FZZ2-AKRBO | PC-222VQXCAX1XSR6FECAL6OP4M | 7/25/2016 17:32 |
| AP-74NSX48N32E7N80NFX884530 | US-WRZZ-0G69V | PC-222KOQ7J4PJEMJY8JFD7AOJI | 7/18/2017 21:28 |

*Fig. 12*

HAPLOTYPE PHASING

HAPLOTYPES
ATACGA
AGCCGC

*Fig. 13A*

GENOTYPE $A \left\{ {T \atop G} \right\} \left\{ {C \atop A} \right\} CG \left\{ {C \atop A} \right\}$

*Fig. 13B*

HIGH THROUGHOUT COST EFFECTIVE SEQUENCING
TECHNOLOGY GIVES GENOTYPES AND NOT HAPLOTYPES.

POSSIBLE   ATACGA   AGACGA
PHASE:     AGCCGC   ATCCGC   . . .

*Fig. 13C*

GENOMIC SERVICES PLATFORM SUPPORTING MULTIPLE APPLICATION PROVIDERS

CLAIM OF PRIORITY

This application claims the benefit of priority, under 35 U.S.C. Section 119(e), to Lu U.S. Provisional Application No. 62/535,781, filed Jul. 21, 2017, entitled "GENOMIC SERVICES PLATFORM SUPPORTING MULTIPLE APPLICATION PROVIDERS," which is incorporated herein by reference in its entirety.

FIELD

This disclosure relates generally to networked systems facilitating the purchase, distribution and use of computer-implemented applications utilizing genomic information obtained from sequencing biological samples.

BACKGROUND

Consumers now have access to genomic tests and services that were recently available only through leading research organizations and clinical laboratories. The decreasing cost of genome sequencing has been one factor in increasing the availability of such direct-to-consumer and personal genomic services. In addition to being less expensive than earlier machines on a per sample basis to perform sequencing, newer sequencing machines are capable of performing sequencing operations much more quickly. Reductions in price further increases the appeal of such services to consumers.

Typically, such genomic services relate not only to laboratory analysis of a person's DNA, but also to algorithms and services relating to genomic data analysis and interpretation of the genomic data. Available genomic services may be directed to, for example, medical testing. The incorporation of DNA data services may enable a consumer to enhance certain experiences, acquire information, or embark on a lifestyle change for improved wellness.

For example, a person concerned with hereditary diseases may utilize one or more services in order to have targeted testing performed (i.e. testing a subset of genes or variants). The results of such medical-related testing could provide clinical information concerning, for example, disease diagnosis, disease predisposition, or carrier status. As another example, a person may also wish to understand whether he or she is lactose intolerant. Other individuals may be interested in identifying forms of exercise which may be recommended for them in some way.

However, in order to take advantage of different genomic services a person generally must go through the process of being sequenced on multiple occasions. This situation stems at least in part from the lack of a widely accessible centralized repository of genomic data for individuals, and from the lack of incentives for commercial and other entities to "share" personal genomic information, even assuming the myriad issues relating to data privacy associated with such sharing could be overcome.

Accordingly, it would be desirable to provide a system enabling consumers to access genomic information and genomic services developed by multiple different entities without having to bear the cost and administrative burden of being sequenced more than once.

SUMMARY

The disclosure pertains to a network-based platform operative to process and store genomic sequence information received from sequencing laboratories or other sources and to provide selected portions of the processed genomic information to third-party application providers having relationships with consumers associated with the genomic sequence information.

In one particular aspect, the disclosure relates to a system for providing genomic services. The system may include genomic sequencing equipment configured to generate initial sequence reads based upon a biological sample obtained from a user (also termed customer or consumer, herein). The system also includes a genomic services platform having a network interface through which the sequence reads are received. The genomic services platform may also include a bioinformatics processing pipeline having a read alignment module, a variant calling module, a variant refinement module, and a variant imputation module. The read alignment module is configured to generate aligned sequence data by aligning the observed sequence reads relative to a reference sequence. The variant calling module is operative to identify observed variants in the aligned sequence data. The variant refinement module may operate to produce a set of refined variants associated with a user and may be configured, by itself or in conjunction with the variant imputation module, to use population reference data in order to: (i) identify additional variants not included in the observed variants and/or (ii) adjust a genotype quality of ones of the observed variants. The genomic services platform also includes genomic data storage containing the set of refined variants and a variant storage module. During operation, the variant storage module may receive a query from network infrastructure of a partner application provider (also termed a "partner" herein) and provide selected ones or sets of the observed, refined, or imputed variants in response to the query. A computing device of the user may include an application in communication with the network infrastructure of the partner application provider.

In another aspect, the disclosure pertains to a system for providing genomic services through a plurality of partner application providers. The system includes genomic sequencing equipment that may be included within one or more sequencing laboratories. The genomic sequencing equipment is configured to generate sequence reads based upon a biological sample obtained from a user. The system further includes a genomic services platform including genomic data storage. The genomic data storage contains aligned sequence data generated by aligning the observed sequence reads relative to a reference sequence and refined variants derived, in one example by using population reference data, from the aligned sequence data. The genomic services platform also includes file storage containing one or more files defining one or more genomic windows respectively associated with each of the plurality of partner application providers, or partner applications. A variant storage module included within the genomic services platform is configured to receive queries provided by the plurality of partner application providers and to fetch, from the genomic data storage, sets of the observed, refined, or imputed variants associated with reference positions included in the one or more genomic windows associated with the respective partner application provider, or partner application. In some examples, one or more "unique" genomic windows or window combinations may be associated with a single application provided by a single partner application provider. The platform may also include a genomics interface through which the set of refined variants are provided to the partner application provider, or streamed to a partner application for example.

BRIEF DESCRIPTION OF THE FIGURES

The invention is more fully appreciated in connection with the following detailed description taken in conjunction with the accompanying drawings, in which:

FIGS. 8A-8D illustrate general examples of some variant imputation operations performed within the bioinformatics processing pipeline 130, according to example embodiments.

FIG. 12 illustrates an example translation or look-up table for a mapping service, according to example embodiments.

FIGS. 13A-13C illustrate aspects of haplotype phasing, according to example embodiments.

Like reference numerals refer to corresponding parts throughout the several views of the drawings.

DETAILED DESCRIPTION OF THE INVENTION

The disclosure pertains to a network-based platform enabling users to purchase or subscribe to products and services that utilize the genomic information of such consumers and are offered by different entities. It is a feature of the disclosed platform that although users may choose from among products and services developed by multiple entities, each user may take advantage of multiple products and services offered through the platform while their genome need not be separately sequenced in connection with use of each such product or service. As is discussed below, once a biological sample provided by a consumer has been sequenced and the resultant genomic information of the consumer has been stored by the platform, the consumer will generally be entitled to purchase or subscribe to various products and services configured to utilize the consumer's genomic information in a digital fashion.

In one embodiment, a consumer may use a computing device (e.g., a smartphone or laptop computer) to download or otherwise obtain a software application developed by a third-party entity having a contractual relationship with an operator of the platform. The consumer may interact with the application, which may result in the application communicating with a network server of the third-party entity. In order to provide services to the consumer, the network server of the third-party entity may request access to one or more selected portions of the genomic information of the consumer stored by the platform. In general, the extent and type of such access may depend upon, for example, the nature of the product or service offered by the third-party entity and the details of the product or subscription level selected by the consumer. In some examples, a third-party entity may be a partner application provider, described more fully below, but this need not necessarily be so.

Figure 1:
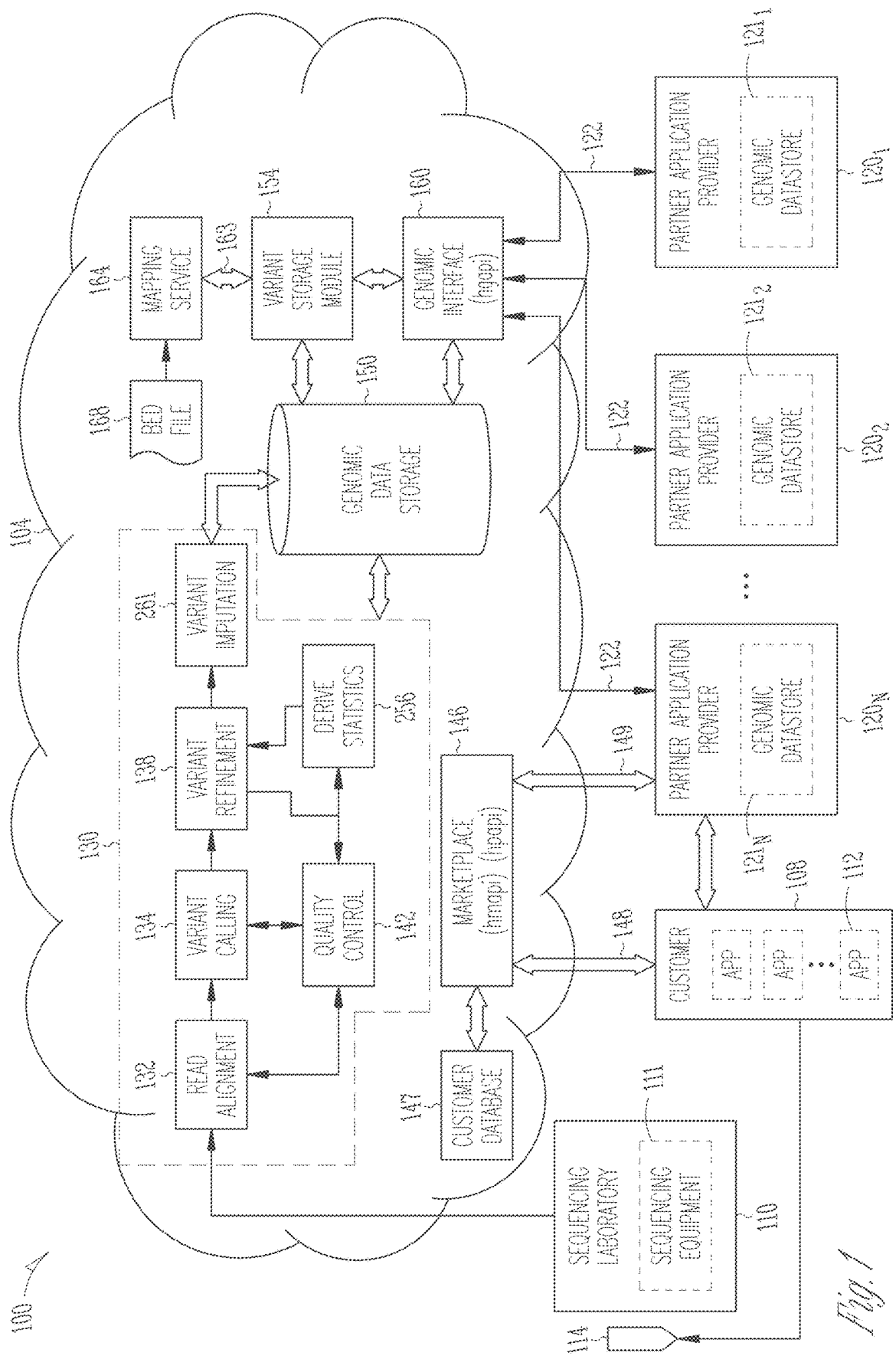
FIG. 1 illustrates a high-level architectural view of a system including a genomic services platform in accordance with the disclosure.

Attention is now directed to FIG. 1, which illustrates a system 100 including a genomic services platform 104 in accordance with the disclosure. As shown, the system includes a sequencing laboratory 110 organized to receive biological samples 114 from consumers. The sequencing laboratory 110 may include next-generation sequencing (NGS) equipment 111 operative to perform sequencing operations upon the biological samples 114 in order to determine genomic sequence information corresponding to such consumers. The resulting genomic sequence information may then be provided to the genomic services platform 104 for data processing, data storage and data access. Such consumers may possess computing devices 108 (e.g., smartphones or laptop computers) storing software applications 112 downloaded or otherwise obtained from servers operated and provided by partner application providers 120. In one embodiment, the genomic services platform 104 is operated by an entity having contractual relationships with each of the partner application providers 120 and may provide such providers with selective access to sets of the consumer genomic information stored by the platform 104.

In the embodiment of FIG. 1, the genomic services platform 104 may be implemented using "cloud" computing capabilities. As is known, cloud computing may be characterized as a model for facilitating on-demand network access to a shared pool of configurable computing resources (e.g., networks, servers, storage, applications, and services) that can be rapidly provisioned and released with minimal management effort or service provider interaction. Cloud systems tend to automatically control resource use by utilizing some form of metering capability with respect to, for example, storage, processing, bandwidth, and active user accounts. Various cloud service models are possible, including cloud software as a service (SaaS), cloud platform as a service (PaaS), and cloud infrastructure as a service (IaaS).

In the embodiment of FIG. 1 the genomic services platform 104 may operate on "private" cloud infrastructure provided and managed by one or more third-party organizations. For example, in the embodiment of FIG. 1 the platform 104 includes a bioinformatics processing pipeline 130 operative in a cloud environment managed by a first third-party organization, with the remainder of the platform 104 operating on infrastructure provided by a second third-party organization. In one embodiment, the bioinformatics processing pipeline 130 operates within the BaseSpace Sequence Hub provided by Illumina and the remainder of the platform 104 operates through an Amazon® Web Service (AWS) Cloud. In other embodiments, some or all of the platform may be implemented using other cloud environments such as, for example, a Microsoft® Azure cloud or another third-party cloud such as DNA Nexus. As shown, the bioinformatics processing pipeline 130 may include a read alignment module 132, a variant calling module 134, a variant refinement module 138, a quality control module 142, and a variant imputation module 261.

In other embodiments, the genomic services platform 104 may be implemented by using on-premise servers and other infrastructure rather than by using cloud-based services. Alternatively, hybrid implementations of the genomic services platform 104 including a combination of on-premise and cloud-based infrastructure are also within the scope of the present disclosure.

Referring again to FIG. 1, the genomics services platform 104 includes a marketplace module 146 for providing a portal through which customers may complete a registration process and optionally purchase applications. In some examples, the marketplace module has access to a customer database 147. The customer database 147 stores data relating to new and existing customers and may be accessed by the marketplace module 146 for customer authorization and credentialing purposes, for example. In some examples, and depending on the services requested, there may be a hand-off of customer data to facilitate the co-ordination of services between the platform 104 and other partner application providers 120, other sequencing laboratories 110, or generally between entities within the system 100.

Through a series of API calls 148 to an API endpoint e.g. Helix™ Marketplace Application Program Interface (HMAPI), a customer's application can invoke certain tasks at the marketplace module 146 to be performed by the marketplace module 146 or in association with other entities within the genomic services platform 104. Typically, tasks using this API will relate to updating consumer data stored in the customer database 147 and may include aspects such as querying data, adding or deleting data, and obtaining metadata about the data. Such applications offered through the portal established by the marketplace module 146 may be the same as, or different from, the applications offered through the partner application providers 120.

Partner application providers can also interact with the marketplace module 146 in relation to non-genomic information. Through a series of API calls 149 to an API endpoint e.g. Helix™ Partner Application Program Interface (HPAPI), a partner application provider 120 can also invoke certain tasks at the marketplace module 146, such as querying customer data, adding or deleting customer data, and obtaining metadata about the customer data.

Again, referring to FIG. 1, upon completing the registration process, in one embodiment a registered customer is sent a receptacle (e.g., a tube or vial) into which the customer may deposit a biological sample 114 (e.g., saliva). In one embodiment, the customer may receive the receptacle via mail or a package delivery service and may send the receptacle containing the biological sample 114 to the sequencing laboratory using the same or a similar mode of delivery. As part of the registration process, the customer may be assigned a unique identifier (such as a unique "user registration ID", a "user ID", a "kitID", or another identifier described further below) that is imprinted or otherwise included on a label attached to the receptacle for the biological sample 114 sent to the customer. The user ID may be in the form of a bar code for tracking progress of the customer's biological sample through the sequencing laboratory 110 and in identifying the customer's sample and related information in the bioinformatics processing pipeline 130. The labeling associated with biological samples 114 sent to the sequencing laboratory typically lacks any personal information enabling direct identification of the customers associated with such samples 114.

In one embodiment, a customer may register via the portal established by the marketplace module 146 prior to ordering genomic-related products or services from partner application providers 120. In other embodiments, the customer may purchase a product directly from a partner application provider 120 and provide registration or purchase information that is then forwarded to the platform 104 via an API endpoint e.g. HPAPI. Upon receiving the registration information, the operator of the platform 104 may send a receptacle to the customer for receiving a biological sample 114, which is subsequently sent by the customer to the sequencing laboratory.

Figure 2:
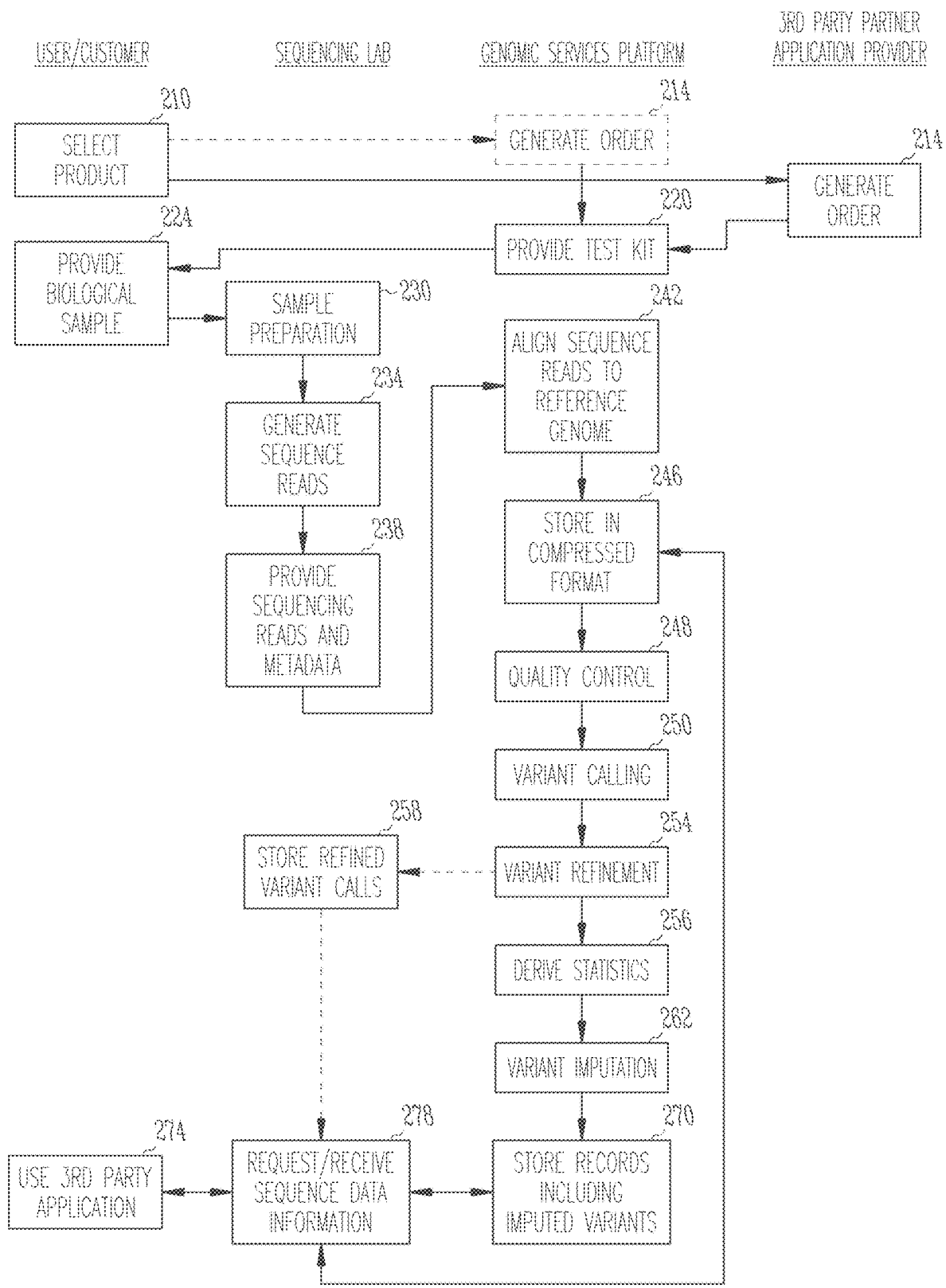
FIG. 2 illustrates an exemplary set of operations performed within the system of FIG. 1.

Attention is now directed to FIG. 2, which illustrates an exemplary set of operations performed within the system 100. As shown, a customer may select a product through either the portal provided by the marketplace module 146 or via a website or the like provided by a partner application provider 120 (stage 210). In response, either the marketplace module 146 or the partner application provider 120 may generate an order (stage 214), which causes a test kit including a receptacle for a biological sample 114 to be sent to the customer (stage 220). The customer then provides the biological sample 114 to the sequencing laboratory 110 (stage 224).

Upon receiving the biological sample 114, the sequencing laboratory prepares the sample for sequencing (stage 230). As part of the preparation process, the sample 114 may be placed in a sample preparation cartridge to which reagents or other substances are added pursuant to the preparation protocol utilized. Such preparation of the sample 114 may include, for example, isolating or purifying the sample 114 and performing one or more of cleaving, degrading, annealing, hybridizing, denaturing, or ligating processes involving the sample 114. These processes may in some examples occur during transit of the sample to the sequencing laboratory 110. Any suitable sample preparation operation known to those of ordinary skill in the art may be employed during stage 230.

Once the biological sample 114 has been prepared, it is processed by sequencing equipment 111 operative to generate observed genomic sequence reads and related quality score information (stage 234). The sequence reads generated may correspond to some or all of the customer's genome sequence including, for example, genomic DNA, cDNA, hnRNA, mRNA, rRNA, tRNA, cRNA and other forms of spliced or modified RNA. In exemplary embodiments, the sequence reads may relate to, for example, somatic, germline, gene expression, and transcriptome sequences.

Figure 4:
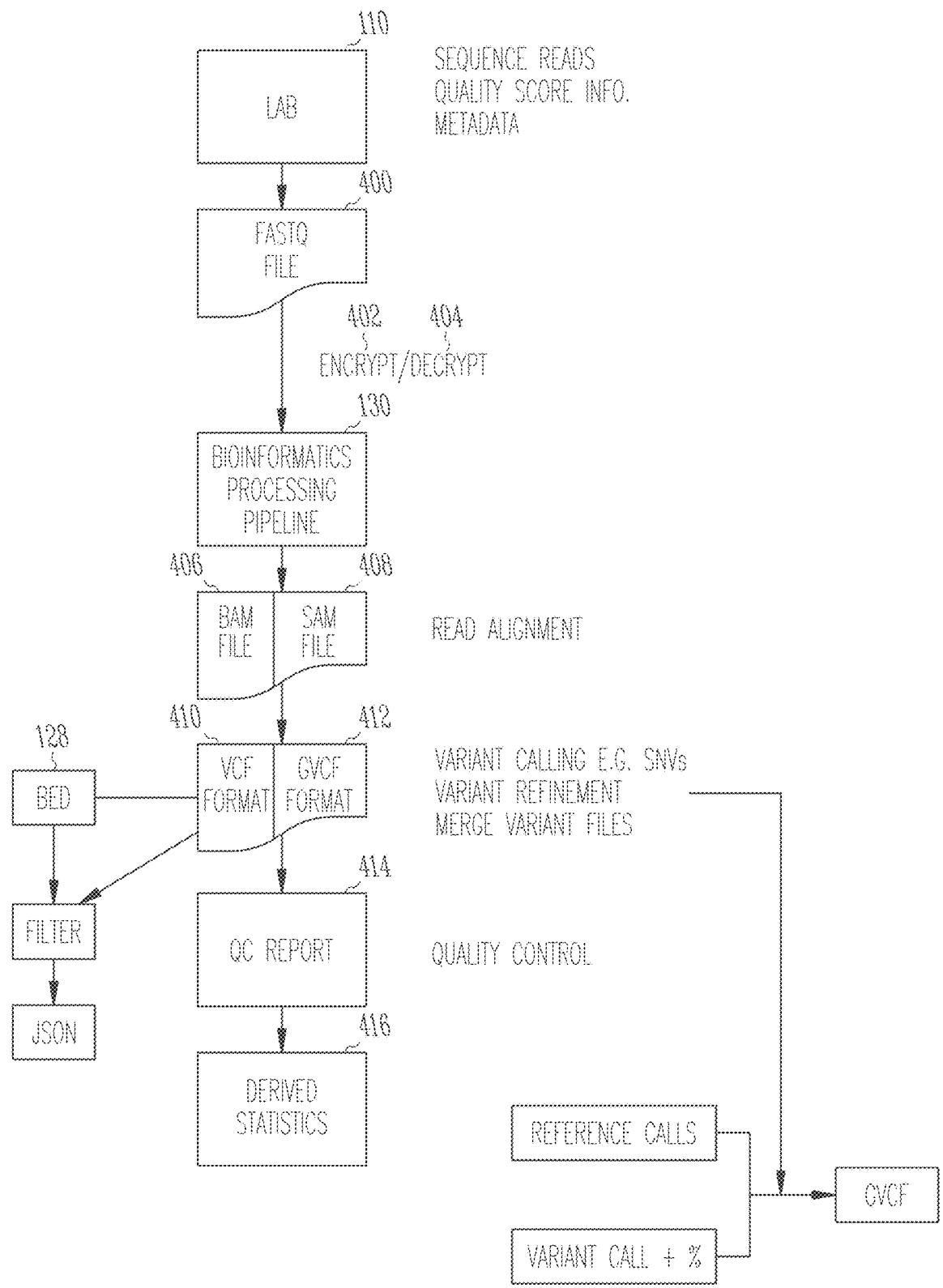
FIG. 4 illustrates a series of operations in a process flow performed by the system of FIG. 1, according to example embodiments.
Figure 5:
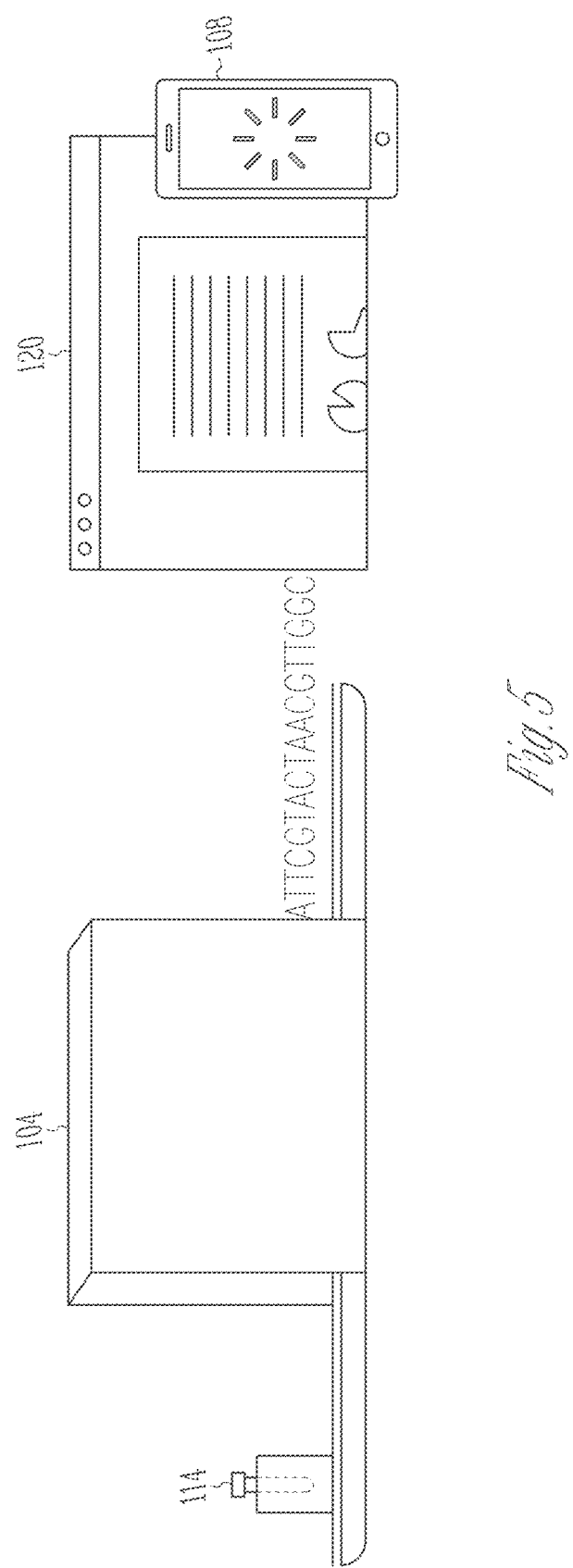
FIG. 5 illustrates a system including a genomic services platform, according to an example embodiment.

With reference to FIG. 4, in one embodiment the sequence reads, related quality score information and certain metadata generated by the sequencing laboratory 110 are included within a storage file 400 (such as a FASTQ file) which is electronically communicated to the bioinformatics processing pipeline 130 (stage 238, FIG. 2). This storage file, or simply the raw sequence reads and related information, may be encrypted at 402 using one or more conventional techniques prior to being communicated to the bioinformatics processing pipeline 130 and subsequently decrypted at 404. For example, the storage file may be encrypted with a symmetric key, which may itself be encrypted.

As is discussed below, and with reference to FIG. 2 and FIG. 4, in one embodiment the bioinformatics processing pipeline 130 uses this information from the sequencing laboratory 110 together with population variation data in order to perform the following operations:
  1. Read Alignment: align the observed sequence reads to the reference genome and store the alignments in a file in a compressed format such as, for example, in a Binary Alignment Map (BAM) file 406, i.e., a binary representation of a Sequence Alignment Map (SAM) file 408 (stages 242, 246, FIG. 2).
  2. Variant Calling: compare the customer's genome to the reference genome and identify variants such as a single nucleotide polymorphisms, insertions, and deletions and store these variants in a file format such as a variant call file 410 (VCF format) or genomic variant call file 412 (GVCF format) (stage 250, FIG. 2).
  3. Variant Refinement: perform additional processing and filtering to derive the final variant calls (stage 254, FIG. 2). In some examples, a ploidy correction is performed during the variant refinement step. Ploidy, in genetics, relates to the number of chromosomes occurring in the nucleus of a cell. A chromosome is a threadlike structure of nucleic acids and protein found in the nucleus of most living cells, carrying genetic information in the form of genes. In normal somatic (body) cells, chromosomes exist in pairs. The condition is called diploidy. During meiosis the cell produces gametes, or germ cells, each containing half the normal or somatic number of chromosomes. This condition is called haploidy. When two germ cells (e.g., egg and sperm) unite, the diploid condition is restored. Polyploidy refers to cells the nuclei of which have three or more times the number of chromosomes found in haploid cells. Some cells have an abnormal number of chromosomes that is not typical for that organism. In some examples, a ploidy correction is performed by making a sex inference using a heuristic based on the ratio of high-quality reads mapped to chromosome Y divided by those mapped to chromosome X.
  4. Quality Control: generate a quality control (QC) report 414 with QC metric values computed on the subject's read alignments and/or variant calls (stage 248, FIG. 2).
  5. Derived Statistics: In one embodiment statistics 416 may be derived based upon, for example, sequence reads and/or variant information for use in quality control and process monitoring. In some alternate examples, a ploidy correction could be performed in this stage instead by making a sex inference using a heuristic based on the ratio of high-quality reads mapped to chromosome Y divided by those mapped to chromosome X (stage 256, FIG. 2). In some examples, derived statistics are obtained as part of the quality control stage, such that statistic derivation is not performed as a discrete, subsequent operation.

Again, referring to FIG. 2, for each of the observed sequence reads in the FASTQ file, the read alignment module 132 determines a corresponding location in a reference sequence (or finds that no such location can be determined) (stage 242). The read alignment module 132 may utilize a mapping algorithm to compare the sequence of a given read to that of the reference sequence and attempt to locate a potentially unique location in the reference sequence that matches the read.

Again, with reference to FIG. 2, the results of the sequence alignment operation may be stored in a compressed-format file such as, for example, in a compressed BAM file (stage 246) or in a file utilizing another compressed storage format. The resulting BAM file may, in one example, be indexed relative to the reference sequence (e.g. a SAM file) and analyzed by the quality control module 142 (stage 248). In one embodiment, the variant calling module 134 is configured to process the BAM file in order to identify the existence of variants such as single nucleotide variants (SNVs) relative to the reference sequence (stage 250). The results of the variant calling process may be stored within, for example, one or more VCF files or in other variant call file formats. In one embodiment, the variant calling module 134 produces two variant data files, although in alternative implementations only a single variant data file may be produced. The first variant data file (e.g. GVCF) provides general information about all sites in the genome, which include both sites with and without variants (reference calls); the second variant data file (e.g. VCF) does not provide information for reference calls. The second variant data file (VCF) provides finalized posterior genotype likelihoods for variants (i.e., for each site at which a variant occurs, it gives the probability that the genotype it assigned to the sample at the site is incorrect). The first variant data file includes genotype likelihoods for variants but they are not finalized as they may be based on incomplete or low-quality information or genotypes. The sequencing and alignment calling process can create many technical artifacts that can lead to inaccurate results. Using various quality metrics computed for the variants, quality filtering is performed on the second variant data file to remove such artifacts. After filtering, the second variant data file is merged with the first variant data file.

In one embodiment, variant refinement (stage 254) is performed with respect to variant and reference calls produced during stage 250 in order to generate a final variant call output of observed variants. As is discussed below, additional variant calls not directly determined by observed results of the sequencing process may be added during a subsequent variant imputation processing step. In some embodiments, for each sample 114 processed during stage 254, the variant refinement module 138 merges the two variant data files generated by the variant calling module 134 for the sample 114 into a single variant data file, merges records in the file that represent adjacent reference calls, merges records in the file that represent overlapping variant calls or reference calls, performs ploidy correction using derived statistics (stage 256), and performs variant filtering. By merging the two files produced by the variant calling module 134, the variant refinement module 138 produces a variant data file with reference calls from the first file and variants calls with posterior genotype likelihoods from the second file. In one embodiment, the variant data file will contain two types of records that can be merged: records representing adjacent reference calls and records representing overlapping variant calls or reference calls.

In some examples, the variant data file containing the refined variant calls produced by the variant refinement module 138 is stored within a genomic data storage 150 before variant imputation and may be encrypted using conventional techniques (stage 258). In one embodiment, the genomic data storage 150 is implemented using cloud-based storage such as, for example, Amazon Simple Storage Service (S3), which is available through Amazon Web Services™ (AWS). In general, S3 provides persistent storage for HTTP access to store and retrieve data.

Figures 6, 7:
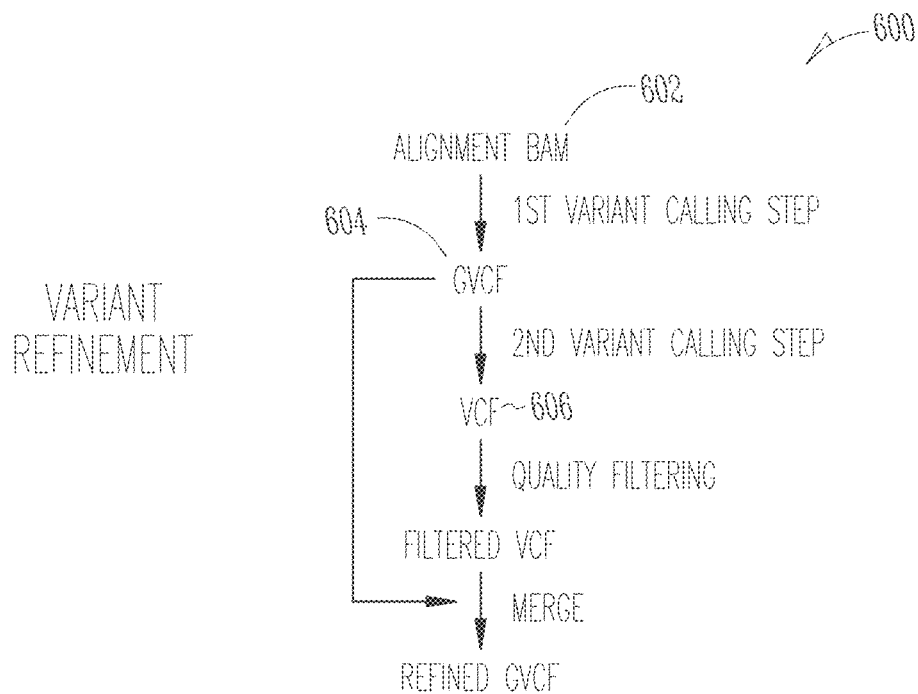
FIG. 6 illustrates a series of operations in a process flow performed by the system of FIG. 1, according to example embodiments.
FIG. 7 illustrates aspects of Browser Extensible Data (BED) file which defines specific regions of a genome, according to an example embodiment.

In other embodiments, with reference to FIG. 6, a variant refinement process 600 is performed after the results of a sequence alignment operation are stored in a compressed-format file such as, for example, a compressed BAM file (stage 602). The process 600 is performed in two phases. In the first phase, an "intermediate" file (GVCF) or "genomic"

VCF file is created (stage 604). The second phase converts the intermediate GVCF file into a VCF file (stage 606). The VCF file format is more widely used for genetic variants so is adopted in this example. The GVCF file is an intermediate file format and not so widely or generally used.

In other embodiments, certain of these variant observation or refinement operations may be omitted or performed in a different order. Other operations facilitating variant observation or refinement may also be performed in lieu of, or in addition to, the foregoing operations.

In some examples, the variant calling module 134 executes a two-step variant calling process through which it identifies sites in the genome where the nucleotide sequences of the aligned reads generated for the sample by the read alignment module 132 differs from the nucleotide sequences in the reference genome they are aligned to, determines the sample's most likely genotype at each site, and computes for each genotype the probability that the genotype is incorrect (i.e. a genotype likelihood). The variant refinement module 138 performs the first step of the variant calling process using, for example, an appropriate implementation of the Broad Institute's Genome Analysis Toolkit (GATK) HaplotypeCaller™. During this step, the module 138 identifies the sites, determines the genotypes, and computes provisional genotype likelihoods. It stores its results in a variant data file that accounts for every position in the genome: for each position, a record in the file establishes whether the position is in a site at which a variant occurs with respect to the reference genome, in which case the record represents a variant call, or not, in which case the record represents a reference call.

The variant calling module 134 performs the second step of the variant calling process using, for example, an appropriate implementation of the GATK GenotypeGVCFs™. During this step, it reads the records in the variant data file from the previous step and performs additional calculations to finalize the genotype likelihoods for each variant call. It stores its results in a variant data file with a record for each variant call.

The variant refinement module 138 performs additional processing on variant and reference calls produced during the variant calling operation 250 to generate the final observed variant call output. Additional un-observed variants calls are added during a later imputation stage discussed further below.

In some examples, using the quality control module 142, the quality of the variant calling for observed or refined variants is assessed. For example, the reproducibility of results using the same sample is compared and checked multiple times. In other examples, an industry call standard can also be used. The standard includes data sets that have been previously analyzed using different technologies and against which the results of real-time variant calling can be compared for concordance, sensitivity, and other aspects. In other examples of quality control, regions of the human genome that are historically known to be difficult to read or to generate inconclusive or "false" variant calls can be "black-listed" and ignored. The difficulty of these regions to read may be caused, for example, by systemic errors such as sequence context processing or aspects related to process chemistry.

In other quality control methods, genome positions are copied, one for male and one for female, for example, and genotypes may be changes to reflect the correct biology. For example, if certain genomic information indicates a customer is a male and should therefore only have one X chromosome, but other test data suggests that there is more than one X chromosome present, this condition and/or the data underlying it is flagged for further inquiry. Other types of flagging are possible. In some examples, a medical oversight board reviews the results of variant calls and makes reviews the acceptability, or not, of results and makes recommendations for improvement. In some examples, variants are classified into classes of thresholds based on quality control results or variant probability information and this information can be shared with partner application providers and customers, accordingly. In other embodiments, certain of these quality control operations may be omitted or performed in a different order. Other operations facilitating quality control may also be performed in lieu of, or in addition to, the foregoing operations.

By way of background, single nucleotide polymorphisms, frequently called SNPs ("snips"), are the most common type of genetic variation among people. Each SNP represents a difference in a single DNA building block, called a nucleotide from a human reference. For example, a SNP may be the replacement of the nucleotide cytosine (C) by the nucleotide thymine (T) in a certain stretch of DNA. SNPs occur normally throughout a person's DNA. They occur once in every 300 nucleotides on average, which means there are roughly ten million SNPs in an individual's genome. Most commonly, these variations are found in the DNA between genes. They can act as biological markers, helping with the location and identification of genes that are associated with disease. When SNPs occur within a gene or in a regulatory region near a gene, they may play a more direct role in disease by affecting the gene's function. Most SNPs have no effect on health or development. Some of these genetic differences, however, have proven to be very important in the study of human health. Researchers have found SNPs that may help predict an individual's response to certain drugs, susceptibility to environmental factors such as toxins, and risk of developing particular diseases. SNPs can also be used to track the inheritance of disease genes within families, and can in some instances be associated with complex diseases such as heart disease, diabetes, and cancer. A single nucleotide variant (SNV) is a difference in a single nucleotide between members of one species without any limitations of frequency and may arise in somatic cells. Some other types of variants include insertion-deletion variants, copy number variants, translocations and transversions.

With reference now to FIGS. 8A-8D, some general examples of variant imputation performed within the bioinformatics processing pipeline 130 are now described. Viewed broadly, genotype imputation is the term used to describe the process of predicting or imputing genotypes that are not directly assayed in a sample of individuals. Genotype imputation may also be seen as the statistical inference of unobserved genotypes which is achieved by combining knowledge of observed genetic variants in an individual with known haplotypes from a population to infer (i.e. identify) the genotype of non-observed loci or to update the likelihood of an observed locus. There are several distinct scenarios in which genotype imputation is desirable, but the term now most often refers to the situation in which a reference panel of haplotypes at a dense set of SNPs (or other variants) is used to impute alleles into a study sample of individuals that have been genotyped at a subset of the SNPs. The goal is to predict the genotypes at the SNPs (or variants) that are not directly observed. These imputed genotypes can then be used to boost the number of SNPs that might be report to a partner application provider 120, for example.

A haplotype is a set of DNA sequences within an organism that was inherited together from a single parent. The word "haplotype" is derived from the word "haploid," which describes cells with only one set of chromosomes, and from the word "genotype," which refers to the genetic makeup of an organism. A haplotype can describe a pair of genes inherited together from one parent on one chromosome, or it can describe all of the genes on a chromosome that were inherited together from a single parent. This group of genes was inherited together because of genetic linkage, or the phenomenon by which genes that are close to each other on the same chromosome are often inherited together. In addition, the term "haplotype" can also refer to the inheritance of a cluster of single nucleotide polymorphisms (SNPs), which are variations at single positions in the DNA sequence among individuals. Generally speaking, by examining haplotypes, scientists can identify patterns of genetic variation that are associated with health and disease states. For instance, if a haplotype is associated with a certain disease, then scientists can examine stretches of DNA near the SNP cluster to try to identify the gene or genes responsible for causing the disease.

In some examples, haplotype reference data is utilized in the variant imputation operation of stage 262 (FIG. 2). A reference haplotype can indicate what types of variants are found at given chromosome positions in a sequence. So, if a chromosome position is known, and a variant is detected at that position but the nature or type of the variant is not known (or is known but with a low degree of certainty or probability), reference to the known variants on the corresponding haplotype position can help to complete or "boost" (or impute) the missing information. Certain missing entries in a sample to be imputed can be completed accordingly.

The output of the variant calling 250 and variant refinement 254 operations described herein is expressed as genotype data. An example representation of a genotype is shown in FIG. 13B of the accompanying drawings. An example set of DNA sequences in a DNA string is shown. The sequences at the locations A, C, and G are known. The identity or sum of the sequences at the locations marked T/G, C/A and C/A appearing in brackets at positions 2, 3, and 6 is known, but the exact location or orientation of them is not. This missing information can be derived by phasing and comparison with human reference data as part of the variant imputation 262 operation.

The genotype data format of FIG. 13B cannot directly be compared against reference haplotype data of the format type shown by example in FIG. 13A. The genotype data is thus first "phased" to generate sample haplotypes that can, in a phased format, be compared against a reference haplotype. Sample phases of this type are shown in FIG. 13C. Each row in a sample phase is derived from the possible, different combinations of genes respectively at the known (A, C and G) positions, and the unknown (or known with low probability), bracketed T/G, C/A and C/A positions shown in FIG. 13B.

Referring now to FIGS. 8A-8D, these views illustrate imputation for a sample of unrelated individuals.

In FIG. 8A, raw input data for the imputation operation includes a set of genotyped SNPs that has a large number of SNPs without any genotype data. Genotype data with missing data at untyped SNPs is shown by the shaded question marks. The variant imputation operation of stage 262 attempts to predict these missing genotypes. Algorithms differ in their details but all essentially involve phasing each individual at the typed SNPs.

Figure 8B:
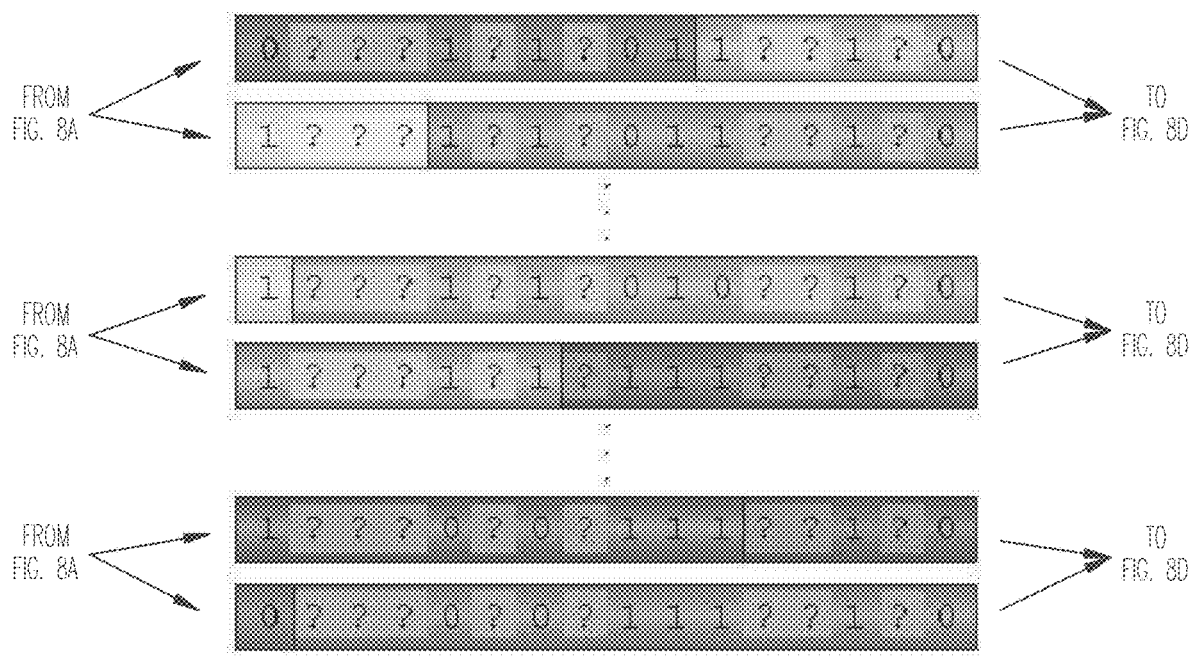

FIG. 8B highlights three phased individuals. Each sample is phased as described above and the resultant haplotypes are modelled as a mosaic of those in a haplotype reference panel of the type shown for example in FIG. 8C.

Figure 8C:

The phased haplotypes are compared to the dense haplotypes in the reference panel (shown in FIG. 8C). The phased study haplotypes are shaded according to which reference haplotypes they match. Thus, most phasing and imputation models that the haplotypes of a given individual are modelled as a mosaic of haplotypes of other individuals.

In FIG. 8D, missing genotypes in the study sample are then imputed using those matching haplotypes in the reference set. The reference haplotypes are used to impute alleles into the samples to create imputed genotypes (shaded). In some examples, the genotypes are imputed and a probability distribution over all three possible genotypes is produced. As discussed below, in some examples this probability is factored into, or even "boosted", in downstream analysis of the imputed data and the merging of certain files containing genomic information.

Referring back to FIG. 2, in one embodiment the variant imputation operation (stage 262) may be performed once the refined variant calls have been generated and optionally stored within genomic data storage 150. In one example, an objective of the variant imputation operation (stage 262) is to perform statistical genotype imputation using population reference data to: (1) report additional variants not observed directly via sequencing reads; and/or (2) boost the genotype quality of low-quality observed variants when the observed genotype agrees with the genotype imputed from population reference data. The variant imputation operation may take as inputs the refined GVCF and/or VCF variant records representing reference blocks, SNVs, and indels discovered by the variant calling module 134, and refined by the variant refinement module 138, for the sample undergoing analysis. Haplotype reference data and reference genome data may be also utilized during stage 262, as discussed above.

Figure 9:
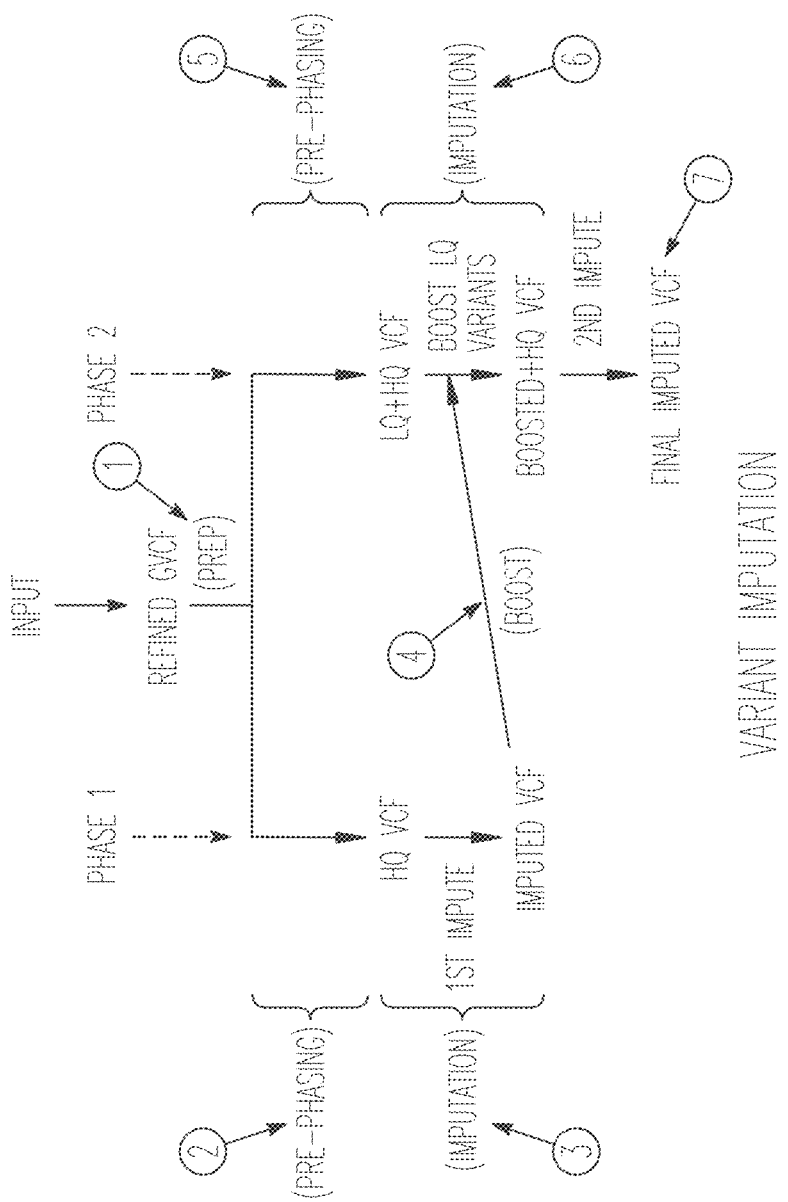
FIG. 9 illustrates further examples of more specific variant imputation operations performed within the bioinformatics processing pipeline 130, according to example embodiments.

With reference to FIG. 9, in one embodiment, the following operations are performed on a "per chromosome" (or per contig) basis during an example variant imputation operation (stage 262, FIG. 2):

1. Prep (or "Pre-processing"): conform the observed data to the reference panel, breaking reference blocks ("ref blocks") where necessary. Reference blocks relate to sequences of "reference calls" (as opposed to "variant calls") i.e. positions where no variant is detected, or a normal result is obtained. Therefore, no imputation is generally required for these locations and the reference blocks can be broken away, or condensed into one or fewer data points, or otherwise handled to reduce processing load. It is a feature of the present methods that the observed (or refined) genotype ("GT") input is separated into high/low-quality ("HQ"/"LQ") genotypes based on genotype quality ("GQ"). A genotype is generally considered to be an HQ genotype when the probability of error is less than 1%. At probabilities of error greater than this, a genotype is considered to be a low-quality (LQ) genotype. In this example, the genotype input data includes a refined GVCF file, for example as shown in the panel in FIG. 10A (discussed further below).
2. Phase 1 (or "Pre-phasing"): pre-phasing using only the high-quality genotypes.
3. Impute 1 (or "Intermediate Imputation"): imputation using phased high-quality haplotypes.

4. Boost (or "Genotype Boosting"): use the Phase 1 imputation output to refine or boost the probability information relating to the low-quality genotypes.
5. Phase 2 (or "Final Pre-phasing"): pre-phasing using the combined (high-quality and boosted) genotypes.
6. Impute 2 (or "Final Imputation"): imputation using the high-quality and boosted haplotypes.
7. Merge: merge the observed and imputed genotypes, generate final imputed VCF file.

The presence of high-quality and low-quality genotypes is an artifact in genomic information obtained by the next generation "sequencing" type of operations described herein because the depth of coverage (i.e. the number of times a base location is observed) can vary across genomic locations. For a given location, the depth of coverage may be at coverage values of 1, 6, or 12, for example. This variance in coverage is known as depth of coverage ("DP"). (For genomic information obtained using "array" methods, this concept of coverage does not exist as data at all positions is read equally).

In some examples, the genotype probability ("GP") of an imputed variant identified in phase 1 (using HQ genotypes only) is used to "boost" (or augment) the genotype probability of a low-quality LQ variant used in phase 2. A given gene position in a genetic sequence may be referred to as a locus. At that locus, a gene includes two alleles which may be represented by a "0" (indicating the allele is the same as the reference allele) or a "1" (indicating a difference, or a variant of the reference allele).

There are three possible genetic combinations for these numbers known as 0/0, 0/1 (the same as 1/0 genetically speaking), and 1/1. In some examples, the probability of three possible (imputed) genotypes existing at a given locus can be expressed by three, respective decimal numbers (or percentages) that, in sum, add up to one (or 100%). For example, (0.96, 0.04, 0=1) or (96%, 4%, 0%=100%) respectively for each of the three possible genotype configurations. In this example, the first and second genotypes (0/0 and 0/1) are more likely to exist.

The series of these three numbers can be referred to as "PL" and relates to the probability of the three possible genotypes respectively occurring at a given locus in a genetic sequence. In some examples, a value for Genotype Quality (GQ) can be derived by taking the difference between the probability values of the two most likely genotypes. In this example, this value might be expressed as 0.92 (or 92%). The confidence that a given imputation is correct can be improved if this "difference" GQ value is relatively high. In other words, when two possible genotype combinations are not closely matched in terms of probability of existence, when only one is possible. It is more helpful when a single imputed combination stands out.

In some examples, the GQ value is expressed on a phred scale. Given a probability $0<p\leq1$, the phred scaled value of $p=-10\log_{10}p$. In some examples, a final probability of an imputed variant existing at a given locus is derived by summing probabilities obtained for the LQ variants in phases 1 and 2 to boost or increase confidence in a determination that a given (imputed) variant does in fact exist where it is suspected to exist. In other words, the dual-phase imputation enables probability information derived in the respective phases to be utilized as corroborating evidence for each other. Expressed in another way, through observation and refinement of the low-quality LQ variants, some direct evidence is derived for their existence, but this evidence is initially not high enough as a probabilistic certainty, or does not reach a certain threshold. Then imputation is performed, though which a secondary or supplementary genotype probability information, for example a GP, can be calculated, i.e. for the probability of the genotype existing at that locus. In instances where the observed (or refined) data "matches" the imputed data (i.e. the genotype or variant appears to be the same under each method), the observed evidence can be combined with the imputed evidence, or boosted, to derive a prediction that is more competent than either when taken alone. There is a lower probability of error.

Figure 10:
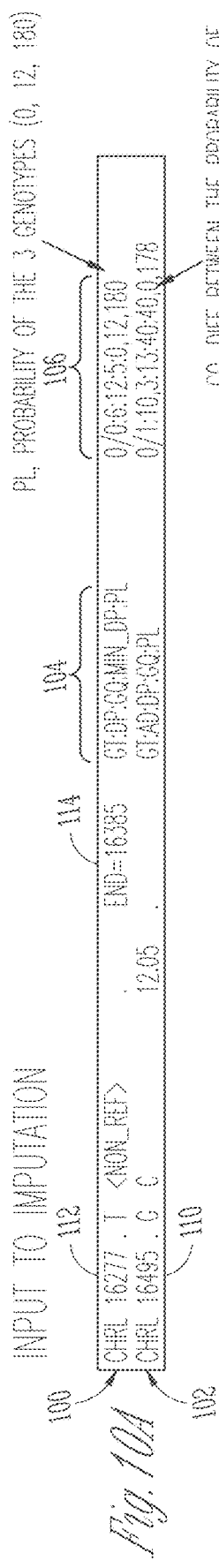
FIGS. 10A-10E illustrate a series of five files or panels utilized in the example variant imputation operations described herein with reference to FIG. 9, according to example embodiments.

Reference is now made to FIGS. 10A-10E. The combined view shows a series of five files or panels respectively marked FIG. 10A through FIG. 10E in the view. The panel in FIG. 10A is a representation of a refined GVCF as an example input to the imputation methods described just above with reference to FIG. 9. Each panel in the series has an upper row 100 and a lower row 102. Each panel also has a format column shown generally at 104. The format column includes "name" fields, such as GT, DP and so forth. Some examples may not include all the following name fields, or may include different name fields. Respective "values" for these name fields appear in a value column shown generally at 106. The illustrated name fields relate to some of the properties discussed above. For example, GT relates to a "genotype", DP relates to a "depth of coverage" (i.e. a number of "reads", and may be expressed as an average of a depth of coverage range of values), GQ relates to "genotype quality" (and may be expressed as a probability on a phred scale for example, and may also be derived by establishing a difference between the probability of the two most likely genotypes), Min_DP relates to a "minimum depth of coverage" (and may be expressed as a minimum value in a range of depth of coverage values), PL relates to a "probability of three genotypes" existing at a given location (and will typically be expressed as a value on a phred scale, or in some examples may be expressed as a series of three respective decimal or percentage numbers), and AD relates to "allele depth" (which may be expressed as two numbers relating to two separate alleles, the sum of which numbers may equal the depth of coverage value).

The upper row 100 in the FIG. 10A panel (in fact, the upper row in each of the five panels) relates to a reference block. This can be ascertained by reference to the value of the GT field in that row, namely 0/0. This value relates to a reference call, not a variant call, as no variant was detected. The reference block extends in a range starting from a position "16277" (shown at 112 in the FIG. 10A panel) and ends at "16385" (shown at 114 in the same panel).

The panel in FIG. 10B is an example representation of an imputation reference panel. The location number or marker "16495" (at 108 in the FIG. 10B panel) of the lower row matches up with the same number, or location, shown at 110 in the FIG. 10A panel and so qualifies as an appropriate reference panel for that location in a gene sequence.

The panel in FIG. 10C is an example output of the "prep" operation 1 described above with reference to FIG. 9. The panel depicts an exemplary prepped VCF file. The values in the upper row of the FIG. 10C panel are the same as the original records in the FIG. 10A panel but the range of the reference block has disappeared and been replaced with a single location (here "16345" at 116 in the FIG. 10C panel) within that range. This is an example of a "breaking" of the reference blocks. Essentially, a single slice of the original reference block is taken at a discrete location in the range as is typically required in imputation methods.

As mentioned above, it is a feature of the present method that the observed (or refined) genotype ("GT") input is separated into high/low-quality ("HQ"/"LQ") genotypes based on genotype quality ("GQ"). A genotype is generally considered to be an HQ genotype when the probability of error is less than 1%. On a phred scale, for example, this value may be expressed as 20. It will be seen that the GQ value in the upper row (at 118) of the FIG. 10C panel is 12 i.e. less than 20, and so this is considered to be a low-quality LQ genotype. Conversely, the GQ value in the lower row (at 120) is 40, and so this is considered to be a high-quality HQ genotype and will be used in the pre-phasing and imputation operations 2 and 3 respectively in phase 1 described above with reference to FIG. 9.

The panel in FIG. 10D is an example representation of the output of operation 3, in other words the result of the imputation using the high-quality variants only. Here, the values in the lower row are exactly the same as the lower row of the FIG. 10C panel, but the upper row includes only the values GT (0/0), and a GP (0.96, 0.04, 0) adding up to 1. These names and values are shown at 122 and 124, respectively. The values signify that the genotype GT (0/0) as a predictive genotype can be predicted with a 96% accuracy (or probability). The GP values thus derived relate to the imputed probability of the three genotypes.

The (imputed) GP value in the FIG. 10D panel can be processed or combined with the (observed) PL probability value in input Panel A to derive a Posterior Genotype Quality ("PGQ") value of 26 seen at 126 in the panel shown in FIG. 10E. Because of the logarithmic nature of the phred scale on which the respective probability values are based in this example, when the respective observed (or refined) and imputed probability values are expressed on that scale, they can be summed to derive a PGQ value. In some examples, PGQ may be calculated from evaluating GQ plus the $\log_{10}$ of the ratio of the probability of the most likely versus the second most likely imputed genotype, i.e. in this example 12 plus $\log_{10}(0.96/0.04)$ yielding a value of approximately 26. Other combinations or permutations are possible. It is to be noted that the GQ value in the upper row of the FIG. 10A panel is 12. This GQ value has been improved to a PGQ value of 26 as shown in the FIG. 10E panel as a result of the improved imputation methods described herein. Genetic information can thus be provided by the platform 104 to a user or a partner application provider 120 with more accuracy and confidence, while reducing processing load, time, and associated cost.

In some embodiments, certain of the operations described above may be omitted or performed in a different order. Other operations facilitating variant imputation may also be performed in lieu of, or in addition to, the foregoing operations. The output of the variant imputation operation of stage 262 may include, for example, variant records representing observed and imputed reference blocks, SNVs, and indels for the sample 114 undergoing analysis. These variant records including refined and imputed variants may then be encrypted using conventional techniques and stored within genomic data storage 150 (stage 270) for controlled access by a customer or partner application provider as described below.

Referring back to FIG. 2, when a customer interacts with an application 112 obtained from a partner application provider 120, the application 112 may make requests to the partner application provider 120 which require the partner application provider to access genomic information stored by the platform 104 (stage 274). Upon receiving such a request, the partner application provider 120 may issue a request for the relevant information through a genomics interface 160 of the platform 104 comprised of a network interface and a genomics API (stage 278). Referring again to FIG. 1, through a series of API calls 122 to an API endpoint e.g. Helix™ Genomics Application Program Interface (HGAPI) at the genomics interface 160, a partner application can invoke certain tasks at the genomics interface 160 such as making requests, querying information, adding, updating or deleting information, and obtaining metadata (tags) about the information.

The various system API's discussed herein (more specifically the example API's described herein as HMAPI, HPAPI and HGAPI) allow a partner application provider to integrate genetics into its applications, products or services. The genomic services platform 104 supports multiple application providers. The API's are designed to use consistent resource-oriented URLs as well as HTTP response codes to indicate errors. They also support built-in HTTP features, such as HTTP verbs, for compatibility with the majority of standard HTTP clients. All responses are returned as JSON messages.

Using the API's, a partner can in some examples access two services based on development needs. Each service has both staging and production endpoints. The two hosted dedicated services can be invoked to notify a partner application provider of user events and to give the partner access to the relevant genetic information that enables DNA-related features. The first service, for example accessible at the endpoint HPAPI, utilizes the customer database 147 and can notify a partner about a customer's status, including aspects such as where the customer's biological sample 114 is in the sequencing process, if they have registered their DNA collection kit, and whether or not they have consented to share their genetic and personal information with the partner's application.

In some examples, the partner API (HPAPI) acts as an interface between the system 100 or platform 104 infrastructure and partner 120 infrastructure. This service can provide certain non-genomic data a partner may need to enable their app to query genomic data and return results back to a customer. In other aspects, the partner API service specifically notifies partners about one or more of the following events: a user has purchased an app and is granting permission for that app to access their genomic data, a user has submitted a saliva sample and that sample is being processed in the lab, a user's sample has completed sequencing and QC (Quality Control) and the genomic data is available to query, a user's genomic data has been updated due to a upgrade or change in the bioinformatics processing pipeline 130, a user has withdrawn consent and/or has funded or removed an app.

Some embodiments of a sample service within the system 100 store and serve sample statuses. With reference to the identifier definitions provided further above, an example sample service can perform, for example, the following functions: translation of inbound accessioning events from partners 120 that contain a kitId and a user ID to a sampleId, translation of outbound (lab 110) sample status (e.g. BaseSpace sample status) with a sampleId to be identified with a kitId and a user ID, storage of sample statuses for retrieval, and publishing message queues to HPAPI or directly to partners on sample status updates.

In one example of an account update provided by the first service, a customer can agree to share his or her relevant genomic and personal information with a partner application, verify an email address, and register a kit. The registration step can be important as a customer purchasing a kit might not be the one submitting it. At the time of purchase, a kit will be sent in the mail and eventually a customer will register that kit. Since the purchaser may be a different person to the sample provider, the customer who delivers genetic data via the spit tube in a kit is not confirmed until that customer registers the kit as their own.

The second service, for example accessible at the endpoint HGAPI, can be used to request the relevant genetic information that enables the partner's DNA-relevant features in its application. Accessing a customer's variants (or markers), for example, is typically a primary use of this service. In some examples, a "no-call" is issued when the genomic services platform 104 is unable to make a call that met a minimum quality threshold due to lack of coverage or poor fit of the probabilistic variant calling model. A no-call is characterized by the presence of a specific entry, such as "−1", in the genotype array. In some examples, a "reference" call is issued when the genomic services platform 104 observes, in sufficient quantity and with sufficient quality, only bases matching the reference sequence. A reference call is characterized by the presence of only "0" entries in the genotype array. In some examples, a "variant" call is issued when the genomic services platform 104 observes, in sufficient quantity and with sufficient quality, bases not matching the reference sequence. A variant call is characterized by the presence of any element in the genotype array greater than 0, representing the presence of an alternative allele present in alternate bases. If the record is not a no-call or a reference call, then it is a variant call.

In some examples, an access token (e.g. OAuth access token) is needed any time a partner application calls a system API to read a customer's information. When a partner requests an OAuth access token, it is required to define token parameters, such as grant type and scope. A partner will need credential pairs to continue, which can be generated by performing appropriate credentialing steps. All API requests are made over HTTPS. Calls made over plain HTTP will fail. API requests without authentication will also fail.

In one embodiment, a request for relevant information from a partner application provider 120 includes a unique ID ("PAC ID" or user ID) that identifies a binary tuple of the form (app, customer), where app is a value identifying one of the applications 112 for the partner application provider 120, and customer is a value identifying the particular user or customer interacting with the application 112 corresponding to the app. In some examples, the PAC ID may comprise a three-part tuple in the form of (partner, app, customer) with corresponding values identifying a partner application provider 120, an application 112, and a customer. Other combinations of values are possible, such as (partner, app). Irrespective of which PAC ID is used, an objective of a PAC ID is to allow a partner application provider 120 to refer to a customer without knowing the actual "value" of the customer and to maintain anonymity and privacy in health records.

In some examples, the PAC ID delimits the type of service and/or data that can provided or accessed. For example, if a customer seeks exercise-related genomics data from one partner application provider 120, and nutrition-related data from another partner application provider, even though the customer value may be the same in both instances, each respective partner application provider is only provided information relating to their respective fields of inquiry. In one embodiment, the genomics API may be configured to enable partner application providers 120 to develop or implement customized encryption for protecting data exchanged with the platform 104.

Customer identification data used by the partner application providers 120 may be different from that used by the other entities discussed herein, for example the sequencing laboratory 110, the genomics services platform 104, and a variant storage module 154 described further below. For example, various user identification elements and formats may be used throughout the system 100, such as a "PAC ID" which is a customer ID for a partner application provider 120. This PAC ID may include a unique UUID (Universal Unique Identifier) which identifies a customer's app purchase and can be used to query HGAPI for a customer's genetic data, such as VCF data, and to separate customer identifying information (such as the user ID) from the customer's genomic data. In further examples, a "user ID" is a unique ID which identifies a genomics services platform 104, bioinformatics processing pipeline 130, or system 100 customer. In still further examples, an "appId" includes a unique UUID identifying a published app in an app store. A standard UUID is typically, but not always, a 128-bit number used to uniquely identify some object or entity on the Internet. Non-standard UUID's are also possible. In further examples, a user may be assigned a "kitID" which is a DNA kit ID. A user may have one or more kitIDs (if, for example, a customer is asked to provide a second saliva sample owing to problems with the first). A "sampleID" uniquely identifies a sample from a kit for the genomics services platform 104, bioinformatics processing pipeline 130, or the lab 110. A mapping between these various ID's can be performed and stored in a mapping service 164, described further below.

In some examples, the mapping service 164 interacts in stage 163 (FIG. 1) with the variant storage module 154 to map customer identification details used by the partner application providers 120 to those used by other parts of the system 100. In some examples, a PAC ID supplied by a partner application provider is used by the variant storage module 154 to identify a customer within the system, perform a look-up of a Browser Extensible Data (BED) file (described further below) associated with the partner's application 112, and map that identification to other customer or sample data, such as the user ID, that may be stored in the same or a different format to the PAC ID. A partner can make a request for genetic data by providing the PAC ID of the customer. The mapping service 164 translates this identifier to the internal IDs for the application and the user. An example of a translation or look-up table supporting the mapping service is shown in FIG. 12. In some examples, in exchanging information between a partner application provider and the variant storage module 154, a customer is known or identified only by their PAC ID. No other identification details are supplied.

Figure 3:
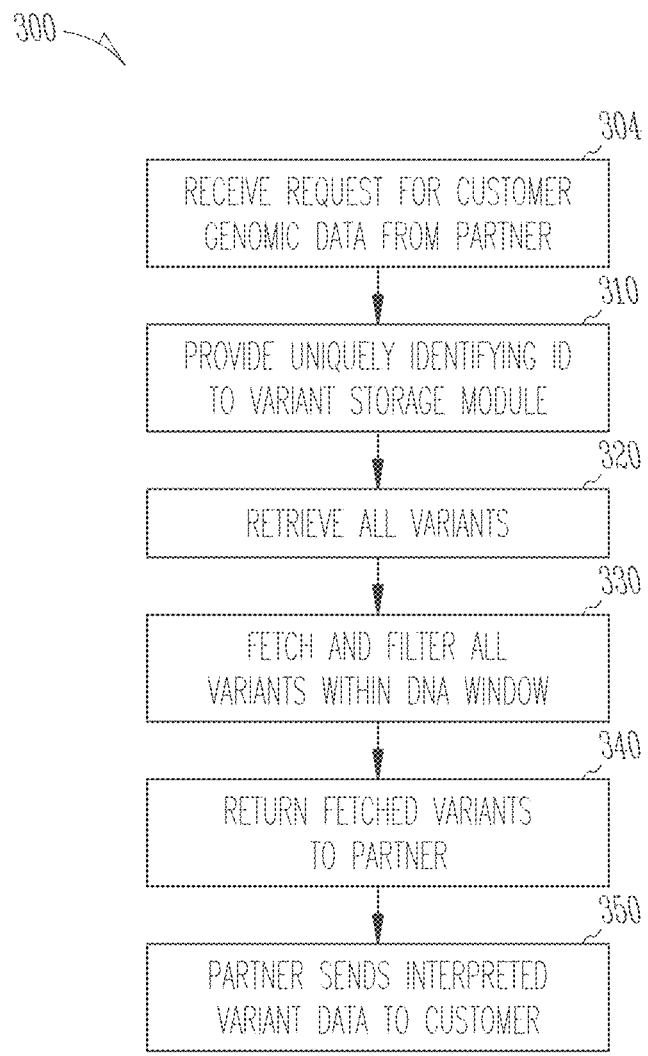
FIG. 3 illustrates a series of operations performed by the system of FIG. 1 in response to a request for genomic information from a partner application provider.

Attention is now directed to FIG. 3, which illustrates a series of operations 300 performed by the system 100 in response to a request for genomic information from the partner application provider 120. Upon receiving the request including the PAC ID (stage 304), the genomics interface 160 may present it to the variant storage module 154 (stage 310).

In one embodiment, the variant storage module 154 operates on a server-less framework in a cloud environment, such as Amazon Web Services (AWS Lambda). The AWS Lambda system allows the variant storage module 154 to run code without provisioning or managing servers. The variant storage module 154 accrues costs only for the compute time it consumes when running its functions. There is no charge when the code is not running. This can be important because call volume demands tend to be highly variable. In some examples, the variant storage module 154 receives in excess of one thousand requests per minute for information. The server-less arrangement is highly scalable and minimizes running costs for the variant storage module 154, and indirectly for partners and customers. Using AWS Lambda, the variant storage module 154 can run code for virtually any type of partner or customer application or backend service with very minimal or zero administration.

In some examples, the variant storage module 154 performs automated tests. The tests are run for any code change that must pass the tests before being deployed to production. For a given PAC ID, the variant storage module 154 may create and output a file and send to HGAPI an expected result that may be investigated if incorrect. In another example, a test (BED) file downloaded from the mapping service 164 is checked for conformity with an expected result. Other automated tests include checking that a request without a user ID (e.g. PAC ID) or app ID, or having a bad PAC ID or app ID, fails. Some data files used within the system may be in a binary variant call format (BCF, or a BAM file described elsewhere herein), and each user may have an associated BCF. Given a BCF, further automated testing may check that filtering by a given region returns correct or expected test intervals, or does not contain a given interval. Other testing may check, again given a BCF file that an open boundary condition is correctly handled, or that overlapping regions are correctly handled, or that compared to a converted VCF, that certain results are expected. Other automated tests may include checking that a (BED) file can be opened correctly, or that if it cannot be opened correctly an error message is thrown. Other testing may check for attempts to open non-existent (BED) files, or to check connectivity with the mapping service 164 such that given an invalid App ID and/or PAC ID, no (BED) file is returned. Other tests include reference block trimming, for example checking that a returned interval is always a subset of the applicable sequence region, or that a reference block that overlaps multiple regions returns correctly each restricted overlapping region. In some examples, the data used for automated tests is dummy data that mimics what real data will look like in production. In other examples, the test data is derived from real biological samples (cell lines) and modified to be used for testing.

Figure 11:
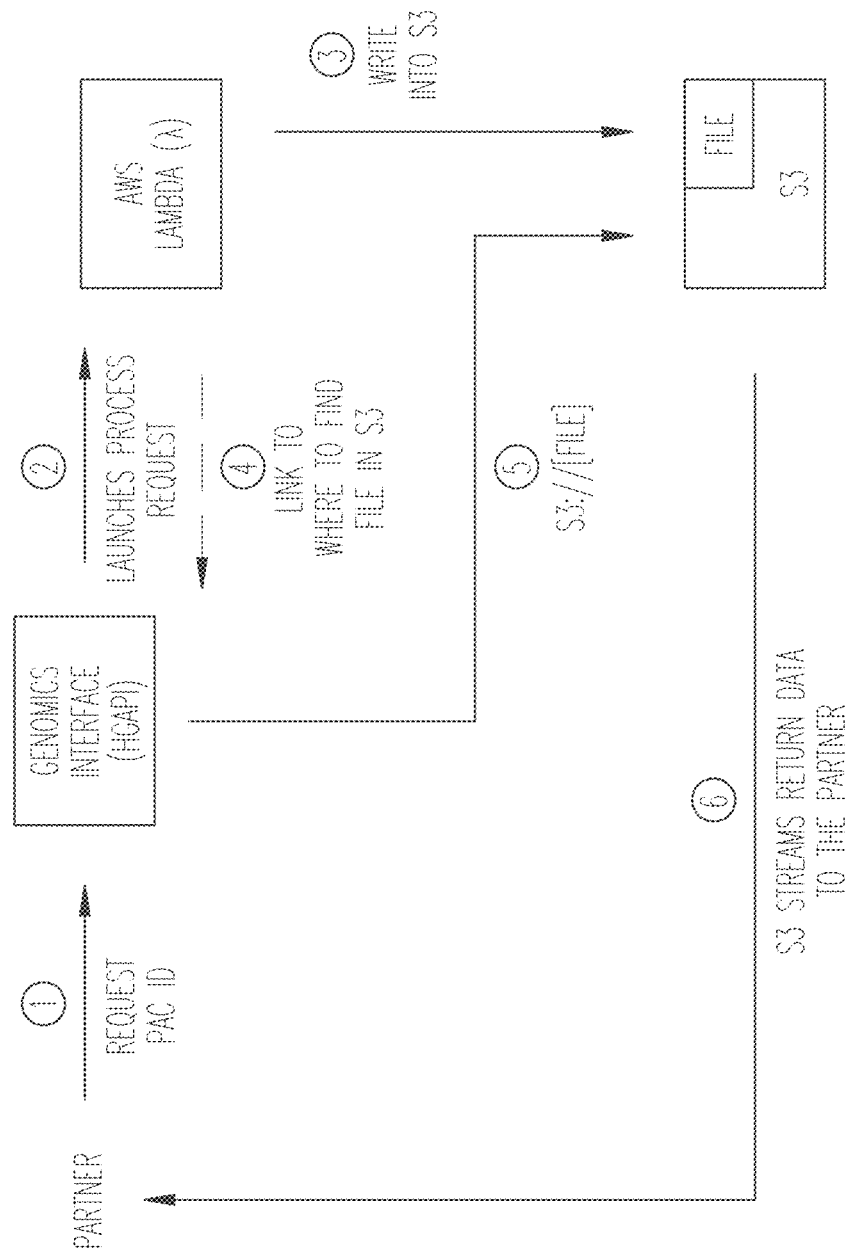
FIG. 11 illustrates a series of operations performed by the system of FIG. 1 in response to a request for genomic information from a partner application provider.

With reference to FIG. 11, in one example, a partner application provider 120 may place a request for information, using the PAC ID (operation 1), via the API 160 (FIG. 1 e.g. HGAPI), and AWS Lambda launches the process request (operation 2). AWS Lambda processes the request and writes the results (operation 3) into cloud-based storage such as, for example, Amazon Simple Storage Service (S3), which is available through Amazon Web Services™ (AWS). In general, S3 provides persistent storage for HTTP access to store and retrieve data. AWS Lambda provides a URL link (operation 4) pointing to this data so that the genomics services platform 104 can access (operation 5) this stored information and pass it on to the relevant partner application provider 120. This may be a synchronous HTTP service. Thus, in response to the initial request for information, S3 can stream the saved data by means of an API such as HGAPI, or even directly, to the partner application provider or a partner application (operation 6). Advantageously, this architecture provides a record of all genomic data provided to a partner, and its flexibility allows this data to be returned either synchronously or asynchronously to a partner application provider 120 or a partner application 112.

In some examples, the variant storage module 154 sets up code to trigger other AWS services automatically or to be called from any web or mobile application. In some examples, the AWS server-less framework enables the variant storage module 154 to apply annotations or "tags" (metadata) to variants when the variants match certain criteria. This service may be requested by a partner application provider. In some examples, the criteria or a tag is applied to a specific window within a (BED) file, discussed further below.

The variant storage module 154 thus includes a server-less process, and in one example the PAC ID and information within a (BED) file 168 (provided by the partner application provider) are used to extract genomic variant information from the genomic data storage 150.

With reference to FIG. 7, a Browser Extensible Data (BED) file 700 defines specific regions of a genome. The file includes, at a minimum, three fields which define a chromosome 702, and a start position 704 and an end position 706 in the genome, respectively. Various conventions may be utilized to specify these locations. In some examples, a (BED) file 168 includes definitions of multiple "DNA windows" defining regions (e.g., one or more ranges of reference locations) of a customer genome that may be accessed by a particular partner application provider 120 or restricted to in support of that partner's application 112. With reference to FIG. 3, upon a request for customer genomic data from a partner application provider via HGAPI, the variant storage module 154 then retrieves all the variants (stage 320) pertaining to a customer's genome and filters these based upon the PAC ID and the appropriate DNA window specified in the (BED) file (stage 330). The fetched variants are then returned via a secure connection to the requesting partner application provider 120 (stage 340), and potentially stored by the requesting partner application provider 120 in an optional genomic datastore 121. This enables the partner application provider 120 to deliver corresponding variant data to the application 112 responsible for initiating the request for genomic information (stage 350). The content of the corresponding variant data will generally be dependent upon the nature of the application 112.

For example, the content could consist of medically-related variant data (e.g., SNPs, indels, insertions, copy number variation, deletions, etc.) in the windowed portion of the customer's genome fetched during stage 330. Such medical-related content could comprise, for example, a disease diagnosis or indication of a predisposition for a particular condition. As another example, the content could comprise personalized content such as, for example, a recommendation for a particular wine or exercise program based upon information supplied by a customer and a different set of characteristics of the windowed portion of the customer's genome.

In another example, referring again to FIG. 4, it will be seen that one output of the bioinformatics processing pipeline 130 is a genomic variant call file GVCF file 412 (after processing of the BAM and SAM files, if any). When a partner application provider 120 or customer requests further genomics information after an initial sequencing, a (BED) file 128 is used, together with a customer's corresponding GVCF file 412, as input to extract genomic variant information from the genomic data storage 150. The extracted variant information is filtered at 130 in accordance with the applicable DNA windows coded in the (BED) file 128, and output in a JSON format. In one example, the JSON-format file has a schema corresponding to the GA4GH (Global Alliance for Genomics and Health) standard. The GA4GH standard API attempts to gather together protocols and data models useful for genomics data interchange. It offers protocols that can be implemented over existing genomics data stores to make these results more easily discovered, shared, and replicated by the partner application providers, for example.

The processes described herein allow a customer's genetic information to be sequenced once, stored indefinitely, and then queried again potentially many times to provide further biogenetic information. Accordingly, a system is provided enabling consumers to access genomic services developed by multiple different entities without having to bear the cost, time-delay inconvenience, and administrative burden of being sequenced more than once.

Thus, in some embodiments, there is provided a system for providing genomic services, the system comprising genomic sequencing equipment wherein the genomic sequencing equipment is configured to generate sequence reads based upon a biological sample obtained from a user; and a genomic services platform, the platform including: a network interface through which are received the sequence reads; a bioinformatics processing pipeline including: a read alignment module configured to generate observed sequence data by aligning the sequence reads relative to a reference sequence; a variant calling module operative to identify observed variants in the observed sequence data; genomic data storage containing the observed variants in the observed sequence data; and a variant storage module disposed to receive a query from network infrastructure of a partner application provider and to provide genomic information based on or derived from the observed variants in response to the query; wherein a computing device of the user includes a partner application in communication with the network infrastructure.

In some examples, the system further comprises a variant refinement module for producing a set of refined variants associated with the user, the variant refinement module being configured to use population reference data in order to at least one of: (i) identify additional variants not included in the observed variants, and (ii) adjust a genotype quality of ones of the observed variants; and wherein the genomic data storage further contains the set of refined variants; and the variant storage module is further disposed to provide selected ones of the set of refined variants in response to the query.

In some examples, the variant refinement module is further configured to adjust a genotype quality of ones of the observed variants when the observed variants correspond to an observed genotype in agreement with a genotype imputed from the population reference data.

In some examples, the genomic services platform further includes file storage including one or more files defining one or more genomic windows associated with the partner application provider or the partner application, and the selected ones of the refined variants are associated with reference locations within at least one of the one or more genomic windows.

In some examples, the system further comprises a variant refinement module for producing a set of refined variants associated with the user; and a variant imputation module for producing a set of imputed variants associated with the user, and configured to use population reference data in order to at least one of: (i) identify additional variants not included in the observed or refined variants, and (ii) adjust a genotype quality of ones of the observed or refined variants when the respective observed or refined variants correspond to a genotype in agreement with a genotype imputed from the population reference data. The variant storage module may be further disposed to provide selected ones of the sets of refined or imputed variants in response to the query.

In another embodiment, a system for providing genomic services comprises: genomic sequencing equipment wherein the genomic sequencing equipment is configured to generate sequence reads based upon a biological sample obtained from a user; and a genomic services platform, the platform including: genomic data storage containing observed sequence data generated by aligning the sequence reads relative to a reference sequence and variants in the observed sequence data derived from the observed sequence data; file storage including one or more files defining one or more genomic windows respectively associated with each of a plurality of partner application providers or partner applications; a variant storage module configured to receive a query provided by one of the plurality of partner application providers or partner applications and to fetch, from the genomic data storage, a set of variants associated with reference positions included in a one of the genomic windows associated with the one of the plurality of partner application providers or partner applications; and a genomic API through which the set of variants are provided to the one of the plurality of partner application providers or partner applications.

The genomic data storage may further contain refined variants derived from the observed sequence data using population reference data.

In some examples, the variant storage module is further configured to fetch, from the genomic data storage, a set of refined variants associated with reference positions included in a one of the genomic windows, and the set of refined variants is provided to the one of the plurality of partner application providers or partner applications through the genomic API.

In some examples, the system further comprises a variant refinement module for producing the set of refined variants associated with the user, the variant refinement module being configured to use population reference data in order to at least one of: (i) identify additional variants not included in variants identified in the observed sequence data, and (ii) adjust a genotype quality of ones of the identified variants.

In some examples, the system further comprises a variant refinement module for producing the set of refined variants associated with the user; and a variant imputation module for producing a set of imputed variants associated with the user, and configured to use population reference data in order to at least one of: (i) identify additional variants not included in the variants derived from the observed sequence data or in the set of refined variants, and (ii) adjust a genotype quality of ones of the variants derived from the observed sequence data or in the set of refined variants when the respective derived or refined variants correspond to a genotype in agreement with a genotype imputed from the population reference data.

In some examples, the variant storage module is further disposed to provide, to the one of the plurality of partner application providers or partner applications, selected ones of the sets of refined or imputed variants in response to the query.

In another embodiment, a genomic services platform for providing genomic services comprises a network interface, in communication with a sequencing laboratory, through which are received genomic sequence reads derived from a biological sample obtained from a user; and a bioinformatics processing pipeline including: a read alignment module configured to generate observed sequence data by aligning the sequence reads relative to a reference sequence; a variant calling module operative to identify observed variants in the observed sequence data; genomic data storage containing at least the observed variants in the observed sequence data; and a variant storage module disposed to receive a query from network infrastructure of a partner application provider and to provide genomic information based on or derived from the observed variants in response to the query.

In some examples, the platform further comprises a variant refinement module for producing a set of refined variants associated with the user, the variant refinement module being configured to use population reference data in order to at least one of: identify additional variants not included in the observed variants, and adjust a genotype quality of ones of the observed variants; and wherein the genomic data storage further contains the set of refined variants; and wherein the variant storage module is further disposed to provide selected ones of the set of refined variants in response to the query.

In some examples, the variant refinement module is further configured to adjust a genotype quality of ones of the observed variants when the observed variants correspond to an observed genotype in agreement with a genotype imputed from the population reference data.

In some examples, the platform further comprises file storage including one or more files defining one or more genomic windows respectively associated with each of a plurality of partner application providers or partner applications and wherein the selected ones of the refined variants are associated with reference locations within one of the one or more genomic windows.

In some examples, the platform further comprises a variant refinement module for producing a set of refined variants associated with the user; and a variant imputation module for producing a set of imputed variants associated with the user, and configured to use population reference data in order to at least one of: (i) identify additional variants not included in the observed or refined variants, and (ii) adjust a genotype quality of ones of the observed or refined variants when the respective observed or refined variants correspond to a genotype in agreement with a genotype imputed from the population reference data.

In some examples, the genomic services platform further includes file storage including one or more files defining one or more genomic windows respectively associated with each of a plurality of partner application providers or partner applications and wherein the selected ones of the refined variants are associated with reference locations within one of the one or more genomic windows, and wherein the variant storage module is further disposed to provide selected ones of the sets of refined or imputed variants in response to the query.

In another embodiment, a genomic services platform for providing genomic services comprises: a network interface through which are received genomic sequence reads derived from a biological sample obtained from a user; a bioinformatics processing pipeline including: a read alignment module configured to generate observed sequence data by aligning the sequence reads relative to a reference sequence; a variant calling module operative to identify observed variants in the observed sequence data; a variant refinement module for producing a set of refined variants associated with the user; a variant imputation module for producing a set of imputed variants associated with the user, the variant imputation module being configured to use population reference data in order to produce the set of imputed variants; and a variant storage module disposed to receive a query from network infrastructure of a partner application provider and to provide selected ones of the refined or imputed variants in response to the query.

In some examples, the variant storage module includes a genomics interface comprising a genomics API endpoint whereby the partner application provider can invoke tasks relating to genomic information comprising at least the selected ones of the refined or imputed variants, and wherein the genomics interface receives a request to invoke a task relating to the genomic information.

In some examples, the variant storage module is further configured to receive, from the partner application provider, via the genomics API endpoint, a user ID including a binary tuple of the form (app, customer), or (partner, app), wherein app is a value identifying an application of the partner application provider, partner is a value identifying the partner application provider, and customer is a value identifying the user interacting with the application corresponding to the app.

In some examples, the variant storage module is further configured to use the user ID supplied by the partner application provider to identify the user and perform a look-up of a Browser Extensible Data (BED) file based on the user ID, the (BED) file defining one or more genomic windows associated with the partner application provider or a partner application, and wherein the selected ones of the refined or imputed variants are associated with reference locations within one of the one or more genomic windows.

In some examples, the variant storage module operates on a server-less framework in a cloud environment without requiring provisioning or managing servers.

In some examples, the platform further comprises a marketplace module comprising a partner API endpoint whereby the partner application provider can invoke tasks, based on the user ID, relating to non-genomic information.

In another embodiment, a genomic services platform for providing genomic services comprises a network interface through which are received genomic sequence reads derived from a biological sample obtained from a user; a bioinformatics processing pipeline including: a read alignment module configured to generate observed sequence data by aligning the sequence reads relative to a reference sequence; a variant calling module operative to identify observed variants in the observed sequence data; a variant refinement module for producing genotype data including a set of refined variants associated with the user; and a variant imputation module for producing a set of imputed variants associated with the user, the variant imputation module being configured to: receive, as input, at least some of the genotype data, and separate the genotype data into high-quality and low-quality genotypes based on a genotype quality.

In some examples, the variant imputation module is further configured to conduct at least a first pre-phasing operation using only the high-quality genotypes to generate phased high-quality haplotypes.

In some examples, the variant imputation module is further configured to conduct at least a first imputation operation using the phased high-quality haplotypes.

In some examples, the variant imputation module is further configured to use an output of the first imputation operation to boost initial probability information relating to the low-quality genotypes to produce boosted genotypes.

In some examples, the variant imputation module is further configured to conduct a second pre-phasing operation using the high-quality genotypes and the boosted genotypes to generate high-quality haplotypes and boosted haplotypes.

In some examples, the variant imputation module is further configured to: conduct a second imputation operation using the high-quality and boosted haplotypes; use an output of the second imputation operation to derive supplementary probability information to relating to the low-quality genotypes; use the initial and supplementary probability information relating to the low-quality genotypes to derive a Posterior Genotype Quality (PGQ) value; merge at least some of the observed or the refined variants with the set of imputed variants; and generate a final imputation file.

In another embodiment, a system for providing genomic services comprises: genomic sequencing equipment wherein the genomic sequencing equipment is configured to: generate sequence reads based upon a biological sample obtained from a user; store the sequence reads in a FASTQ storage file; and communicate the FASTQ file electronically to a recipient; a genomic services platform, the platform including: a network interface through which are received the sequence reads; a bioinformatics processing pipeline, the bioinformatics processing pipeline including: a read alignment module configured to: receive the FASTQ file from the genomic sequencing equipment and use data contained therein to generate observed sequence data by aligning the sequence reads relative to a reference sequence; and store the alignments in a file in a compressed format; a variant calling module operative to: identify observed variants in the observed sequence data, the variants including one or more of a single nucleotide polymorphism, an insertion, and a deletion; and store the observed variants in a variant calling file (VCF) format, or a genomic variant call file (GVCF) format; and a variant refinement module for producing a set of refined variants associated with the user, genomic data storage containing the set of refined variants; and a variant storage module disposed to receive a query from network infrastructure of a partner application provider and to provide selected ones of the refined variants in response to the query.

In some examples, the read alignment module utilizes a mapping algorithm to compare the sequence of a given read to that of the reference sequence to locate a potentially unique location in the reference sequence that matches the read.

In some examples, the read alignment module is further configured to store the alignments in a compressed format in a Binary Alignment Map (BAM) file, and index the BAM file relative to the reference sequence to generate a Sequence Alignment Map (SAM) file.

In some examples, the variant calling module is further operative to process the BAM (or SAM) file to identify the existence of the observed variants in the observed sequence data.

In some examples, the variant calling module is further operative to produce at least two variant data files, the at least two variant data files including: a first genomic variant data file (GVCF) providing genomic information about all sites in the sequence reads obtained from the user genome, the sites including both sites with variants and reference call sites without variants; and a second variant data file (VCF) providing genomic information about sites in the sequence reads obtained from the user genome, the genomic information including posterior genotype likelihoods for sites with variants, but not including information about reference call sites without variants.

In some examples, the variant refinement module is operative to merge the first GVCF and second VCF files to produce a single variant call file, the single variant call file including reference calls from the first GVCF file and variants calls with posterior genotype likelihoods from the second VCF file.

In some examples, the genomic services platform further includes file storage including one or more Browser Extensible Data (BED) files defining one or more genomic windows associated with the partner application provider or a partner application, and wherein the selected ones of the refined variants are associated with reference locations within one of the one or more genomic windows.

In another embodiment, a genomic services platform for providing genomic services comprises a network interface through which are received genomic sequence reads derived from a biological sample obtained from a user; a bioinformatics processing pipeline including: a read alignment module configured to receive a genomics file from genomic sequencing equipment and use data contained therein to generate observed sequence data by aligning the sequence reads relative to a reference sequence; a variant calling module operative to identify observed variants in the observed sequence data, and store the observed variants in a variant calling file; a variant refinement module for producing genotype data including a set of refined variants associated with the user; and a variant imputation module for producing a set of imputed variants associated with the user, the variant imputation module being configured to receive, as input, at least some of the genotype data, and separate the genotype data into high-quality and low-quality genotypes based on a genotype quality.

In some examples, the variant imputation module conducts at least a first pre-phasing operation using only the high-quality genotypes to generate phased high-quality haplotypes.

In some examples, the variant imputation module conducts at least a first imputation operation using the phased high-quality haplotypes.

In some examples, the variant imputation module uses an output of the first imputation operation to boost initial probability information relating to the low-quality genotypes to produce boosted genotypes.

In some examples, the variant imputation module conducts a second pre-phasing operation using the high-quality genotypes and the boosted genotypes to generate high-quality haplotypes and boosted haplotypes.

In some examples, the variant calling module produces at least two variant data files, the at least two variant data files including: a first genomic variant data file (GVCF) providing genomic information about all sites in the sequence reads, the sites including both sites with variants and reference call sites without variants; and a second variant data file (VCF) providing genomic information about sites in the sequence reads, the genomic information including posterior genotype likelihoods for sites with variants, but not including information about reference call sites without variants, and wherein the variant imputation module: conducts a second imputation operation using the high-quality and boosted haplotypes; uses an output of the second imputation operation to derive supplementary probability information to relating to the low-quality genotypes; uses the initial and supplementary probability information relating to the low-quality genotypes to derive a posterior genotype quality value; merges at least some of the observed or the refined variants with the set of imputed variants; and generates a final imputation file, the final imputation file including at least some of the genetic information stored in the second variant data file (VCF), and at least one posterior genotype quality value.

In another embodiment, a genomic services platform for providing genomic services comprises a network interface through which are received genomic sequence reads derived from a biological sample obtained from a user; a bioinformatics processing pipeline including: a read alignment module configured to generate observed sequence data by aligning the sequence reads relative to a reference sequence; a variant calling module operative to identify observed variants in the observed sequence data; a variant refinement module for producing a set of refined variants associated with the user; a variant imputation module for producing a set of imputed variants associated with the user, the variant imputation module being configured to use population reference data in order to produce the set of imputed variants; and a variant storage module, operating on a server-less framework, disposed to receive a query from network infrastructure of a partner application provider and to provide selected ones of the refined or imputed variants in response to the query.

In some examples, the variant storage module includes a genomics interface comprising a genomics API endpoint whereby the partner application provider can invoke tasks relating to genomic information comprising at least the selected ones of the refined or imputed variants, and wherein the genomics interface receives a request to invoke a task relating to the genomic information.

In some examples, the variant storage module is further configured to receive, from the partner application provider, via the genomics API endpoint, a user ID including a binary tuple of the form (app, customer), or (partner, app), wherein app is a value identifying an application of the partner application provider, partner is a value identifying the partner application provider, and customer is a value identifying the user interacting with the application corresponding to the app.

In some examples, the variant storage module is further configured to use the user ID supplied by the partner application provider to identify the user within the bioinformatics processing pipeline and perform a look-up of a Browser Extensible Data (BED) file based on the user ID, the (BED) file defining one or more genomic windows associated with the partner application provider or a partner application, and wherein the selected ones of the refined or imputed variants are associated with reference locations within one of the one or more genomic windows.

In some examples, the variant storage module is further disposed to provide, in response to the query, to the partner application provider or partner application, selected ones of the refined or imputed variants asynchronously, and wherein data streams including genomic information can be returned synchronously to the partner application provider or partner application.

In some examples, the platform further comprises a marketplace module comprising a partner API endpoint whereby the partner application provider can invoke tasks, based on the user ID, relating to non-genomic information.

Figure 14:
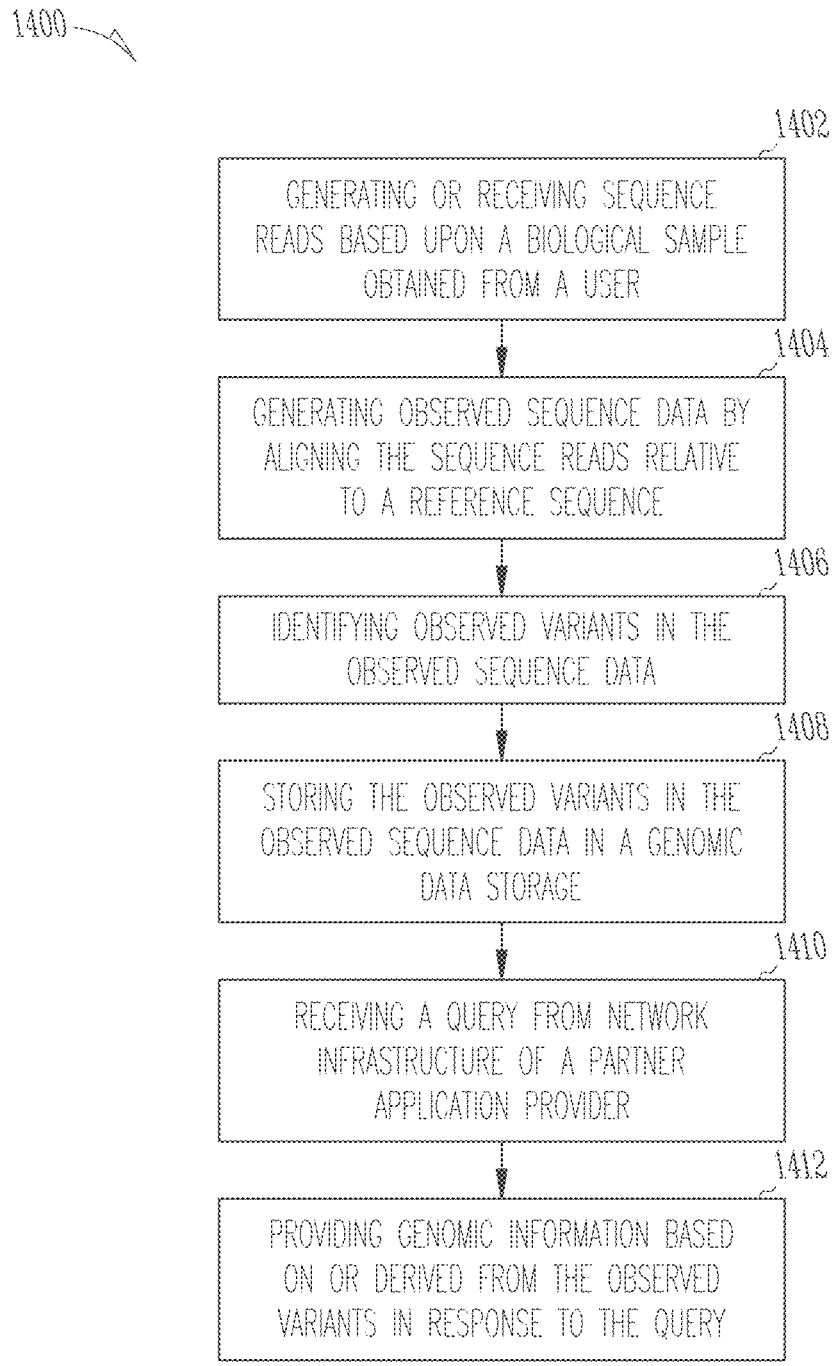
FIGS. 14-21 illustrate exemplary flowcharts for methods for providing genomic services, according to example embodiments.

Some embodiments of the present inventive subject matter include methods for providing genomic services. A flow diagram for one example method 1400 is illustrated in FIG. 14. The method 1400 includes: at block 1402, generating or receiving sequence reads based upon a biological sample obtained from a user; at block 1404, generating observed sequence data by aligning the sequence reads relative to a reference sequence; at block 1406, identifying observed variants in the observed sequence data; at block 1408, storing the observed variants in the observed sequence data in a genomic data storage; at block 1410, receiving a query from network infrastructure of a partner application provider; and at block 1412, providing genomic information based on or derived from the observed variants in response to the query.

The method 1400 may further comprise producing a set of refined variants associated with the user using population reference data in order to at least one of: identify additional variants not included in the observed variants, and adjust a genotype quality of ones of the observed variants; storing the set of refined variants in the genomic data storage; and providing selected ones of the set of refined variants in response to the query.

The method 1400 may further comprise adjusting a genotype quality of ones of the observed variants when the observed variants correspond to an observed genotype in agreement with a genotype imputed from the population reference data.

The method 1400 may further comprise including, in a file storage, one or more files defining one or more genomic windows associated with the partner application provider or a partner application, wherein the selected ones of the refined variants are associated with reference locations within at least one of the one or more genomic windows.

The method 1400 may further comprise producing a set of refined variants associated with the user; and producing a set of imputed variants associated with the user by using population reference data in order to at least one of: identify additional variants not included in the observed or refined variants, and adjust a genotype quality of ones of the observed or refined variants when the respective observed or refined variants correspond to a genotype in agreement with a genotype imputed from the population reference data.

The method 1400 may further comprise providing selected ones of the sets of refined or imputed variants in response to the query.

Figure 15:
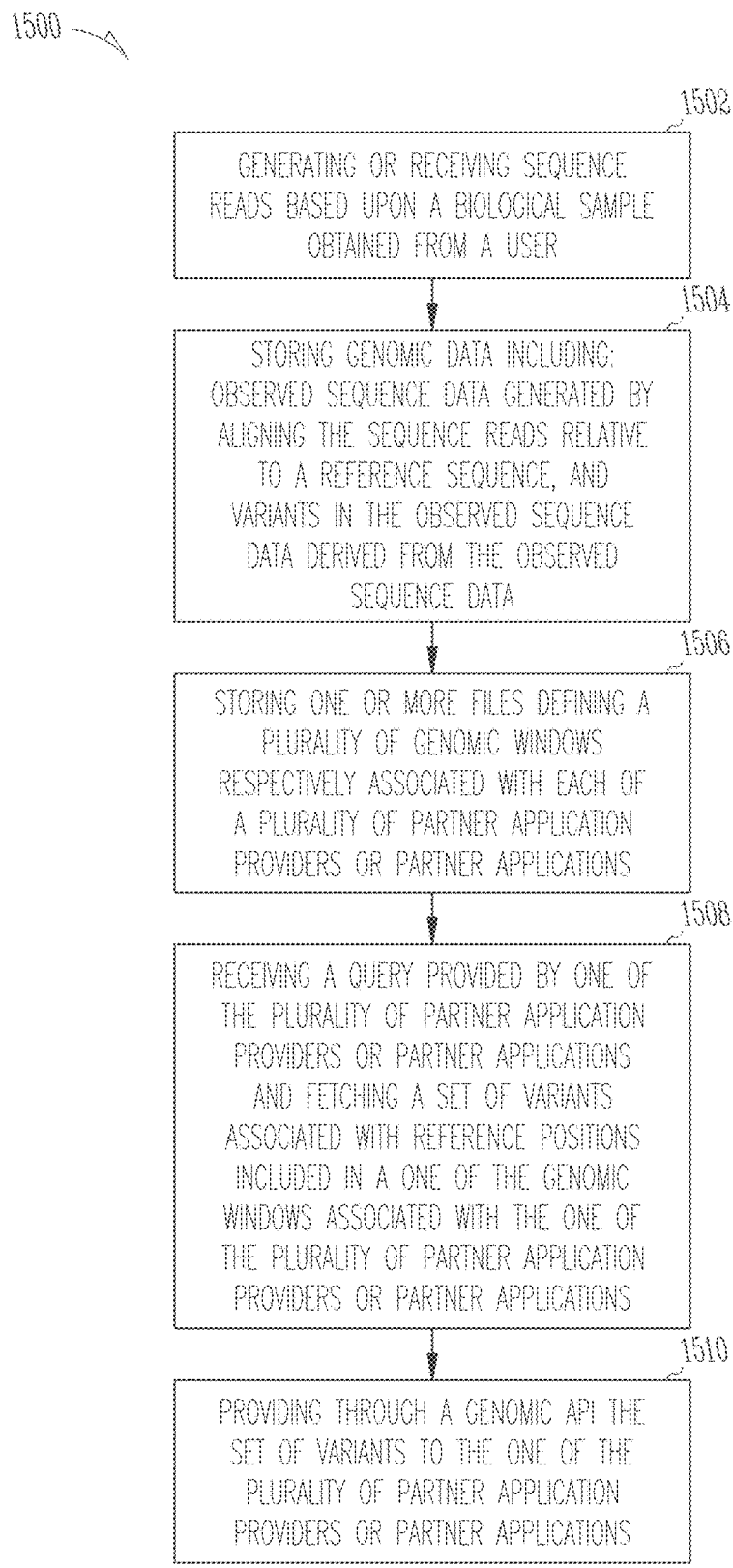

A flow diagram for another example method 1500 is illustrated in FIG. 15. The method 1500 includes: at block 1502, generating or receiving sequence reads based upon a biological sample obtained from a user; at block 1504, storing genomic data including: observed sequence data generated by aligning the sequence reads relative to a reference sequence, and variants in the observed sequence data derived from the observed sequence data; at block 1506, storing one or more files defining a plurality of genomic windows respectively associated with each of a plurality of partner application providers or partner applications; at block 1508, receiving a query provided by one of the plurality of partner application providers or partner applications and fetching a set of variants associated with reference positions included in a one of the genomic windows associated with the one of the plurality of partner application providers or partner applications; and, at block 1510, providing through a genomic API the set of variants to the one of the plurality of partner application providers or partner applications.

In some examples, storing the genomic data further includes storing refined variants derived from the observed sequence data using population reference data.

The method 1500 may further comprise fetching a set of refined variants associated with reference positions included in a one of the genomic windows, and providing the set of refined variants to the one of the plurality of partner application providers or partner applications through the genomic API.

The method 1500 may further comprise producing the set of refined variants associated with the user by using population reference data in order to at least one of: (i) identify additional variants not included in variants identified in the observed sequence data, and (ii) adjust a genotype quality of ones of the identified variants.

The method 1500 may further comprise producing the set of refined variants associated with the user; and producing a set of imputed variants associated with the user by using population reference data in order to at least one of: (i) identify additional variants not included in the variants derived from the observed sequence data or in the set of refined variants, and (ii) adjust a genotype quality of ones of the variants derived from the observed sequence data or in the set of refined variants when the respective derived or refined variants correspond to a genotype in agreement with a genotype imputed from the population reference data.

The method 1500 may further comprise providing, to the one of the plurality of partner application providers or partner applications, selected ones of the sets of refined or imputed variants in response to the query.

Figure 16:
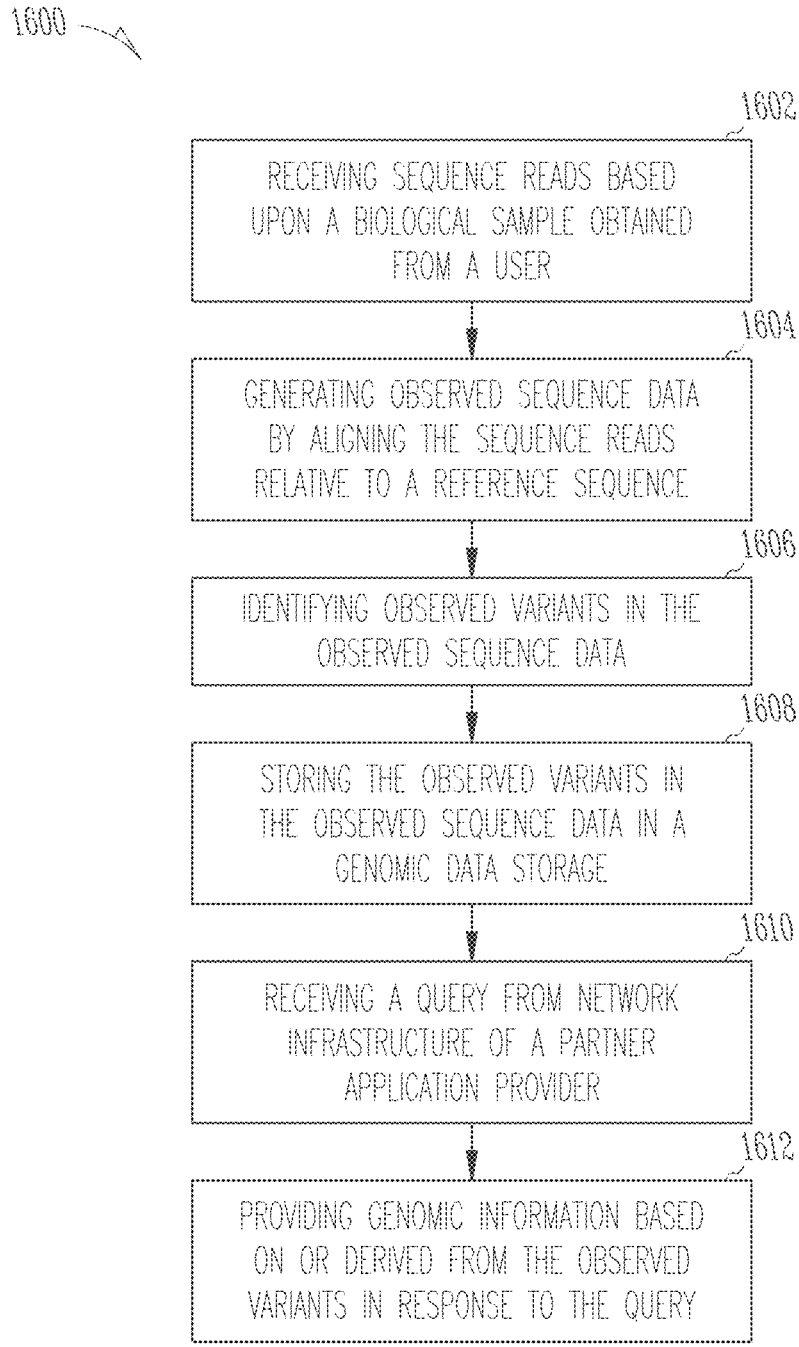

A flow diagram for another example method 1600 is illustrated in FIG. 16. The method 1600 includes: at block 1602, receiving sequence reads based upon a biological sample obtained from a user; at bock 1604, generating observed sequence data by aligning the sequence reads relative to a reference sequence; at block 1606, identifying observed variants in the observed sequence data; at block 1608, storing the observed variants in the observed sequence data in a genomic data storage; at block 1610, receiving a query from network infrastructure of a partner application provider; and, at block 1612, providing genomic information based on or derived from the observed variants in response to the query.

The method 1600 may further comprise producing a set of refined variants associated with the user using population reference data in order to at least one of: identify additional variants not included in the observed variants, and adjust a genotype quality of ones of the observed variants; storing the set of refined variants in the genomic data storage; and providing selected ones of the set of refined variants in response to the query.

The method 1600 may further comprise adjusting a genotype quality of ones of the observed variants when the observed variants correspond to an observed genotype in agreement with a genotype imputed from the population reference data.

The method 1600 may further comprise including, in a file storage, one or more files defining one or more genomic windows respectively associated with each of a plurality of partner application providers or partner applications, and wherein the selected ones of the refined variants are associated with reference locations within one of the one or more genomic windows.

The method 1600 may further comprise producing a set of refined variants associated with the user; and producing a set of imputed variants associated with the user by using population reference data in order to at least one of: identify additional variants not included in the observed or refined variants, and adjust a genotype quality of ones of the observed or refined variants when the respective observed or refined variants correspond to a genotype in agreement with a genotype imputed from the population reference data.

The method 1600 may further comprise including, in a file storage, one or more files defining one or more genomic windows respectively associated with each of a plurality of partner application providers or partner applications and wherein the selected ones of the refined variants are associated with reference locations within one of the one or more genomic windows; and providing selected ones of the sets of refined or imputed variants in response to the query.

Figure 17:
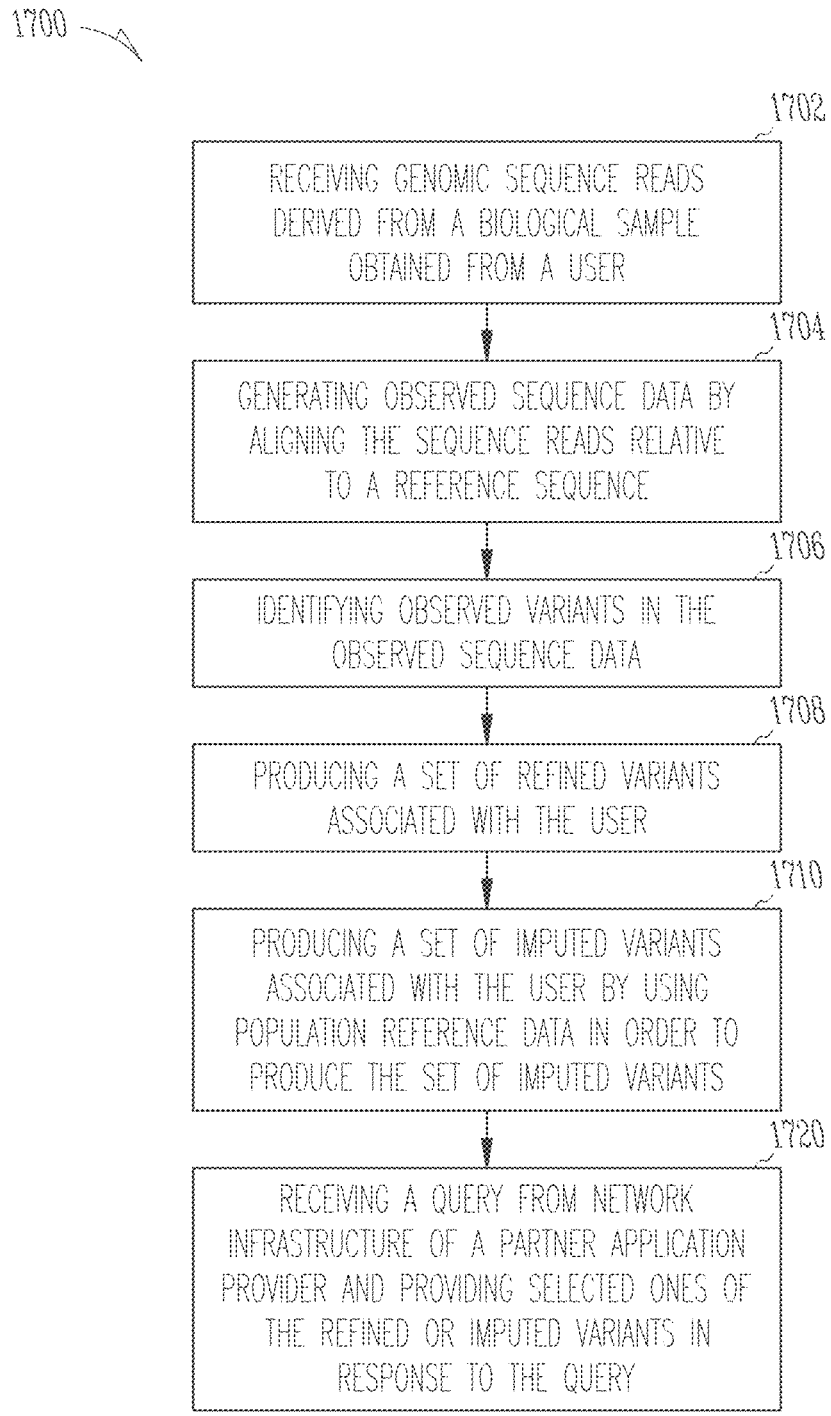

A flow diagram for another example method 1700 is illustrated in FIG. 17. The method 1700 includes: at block 1702, receiving genomic sequence reads derived from a biological sample obtained from a user; at block 1704, generating observed sequence data by aligning the sequence reads relative to a reference sequence; at block 1706, identifying observed variants in the observed sequence data; at block 1708, producing a set of refined variants associated with the user; at block 1710, producing a set of imputed variants associated with the user by using population reference data in order to produce the set of imputed variants; and at block 1720, receiving a query from network infrastructure of a partner application provider and providing selected ones of the refined or imputed variants in response to the query.

The method 1700 may further comprise providing a genomics interface comprising a genomics API endpoint whereby the partner application provider can invoke tasks relating to genomic information comprising at least the selected ones of the refined or imputed variants, and receiving a request to invoke a task relating to the genomic information.

The method 1700 may further comprise receiving, from the partner application provider, via the genomics API endpoint, a user ID including a binary tuple of the form (app, customer), or (partner, app), wherein app is a value identifying an application of the partner application provider, partner is a value identifying the partner application provider, and customer is a value identifying the user interacting with the application corresponding to the app.

The method 1700 may further comprise using the user ID supplied by the partner application provider to identify the user and performing a look-up of a Browser Extensible Data (BED) file based on the user ID, the (BED) file defining one or more genomic windows associated with the partner application provider or a partner application, and wherein the selected ones of the refined or imputed variants are associated with reference locations within one of the one or more genomic windows.

In some examples, receiving a query from network infrastructure of a partner application provider and providing selected ones of the refined or imputed variants in response to the query is performed in a server-less framework in a cloud environment without requiring provisioning or managing servers.

The method 1700 may further comprise providing a marketplace module comprising a partner API endpoint whereby the partner application provider can invoke tasks, based on the user ID, relating to non-genomic information, and receiving a request to invoke a task relating to the non-genomic information.

Figure 18:
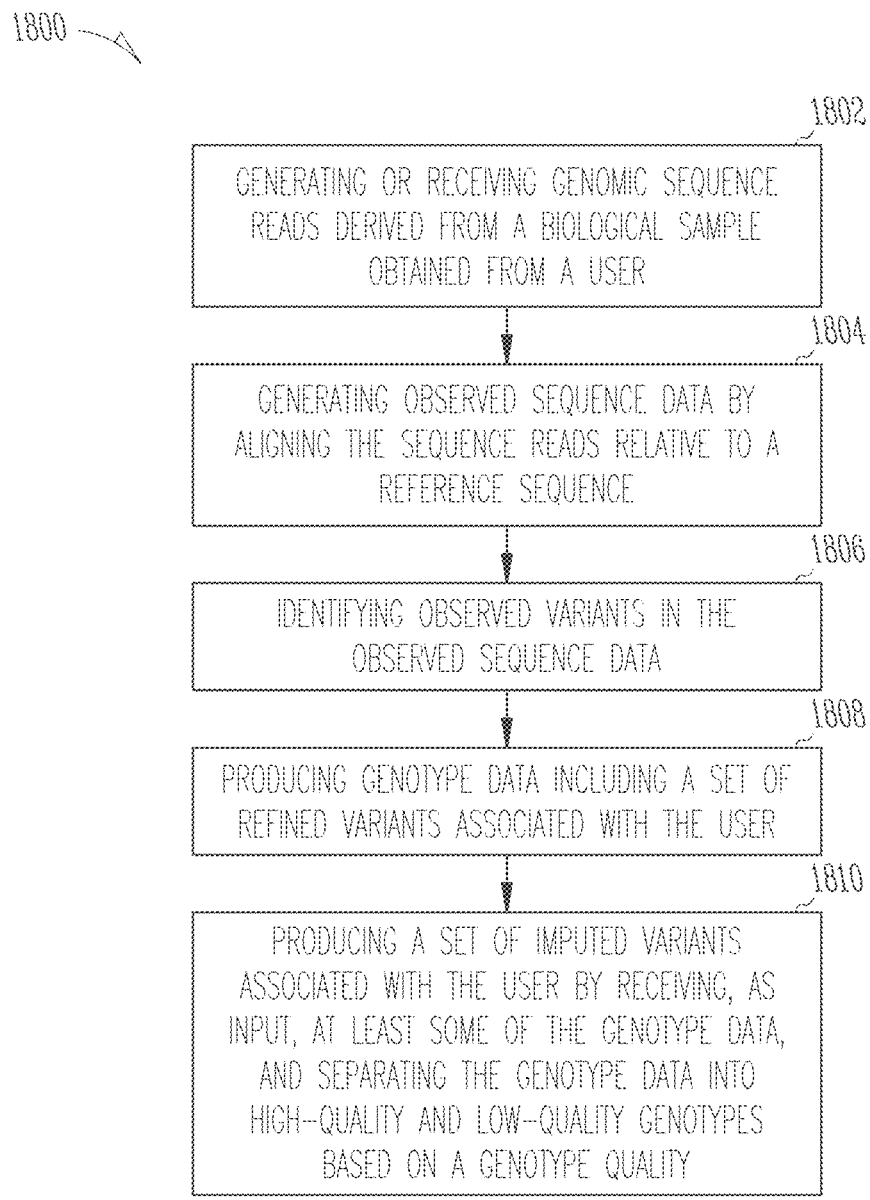

A flow diagram for another example method 1800 is illustrated in FIG. 18. The method 1800 includes: at block 1802, generating or receiving genomic sequence reads derived from a biological sample obtained from a user; at block 1804, generating observed sequence data by aligning the sequence reads relative to a reference sequence; at block 1806, identifying observed variants in the observed sequence data; at block 1808, producing genotype data including a set of refined variants associated with the user; at block 1810, producing a set of imputed variants associated with the user by: receiving, as input, at least some of the genotype data, and separating the genotype data into high-quality and low-quality genotypes based on a genotype quality.

The method 1800 may further comprise conducting at least a first pre-phasing operation using only the high-quality genotypes to generate phased high-quality haplotypes.

The method 1800 may further comprise conducting at least a first imputation operation using the phased high-quality haplotypes.

The method 1800 may further comprise using an output of the first imputation operation to boost initial probability information relating to the low-quality genotypes to produce boosted genotypes.

The method 1800 may further comprise conducting a second pre-phasing operation using the high-quality genotypes and the boosted genotypes to generate high-quality haplotypes and boosted haplotypes.

The method 1800 may further comprise conducting a second imputation operation using the high-quality and boosted haplotypes; using an output of the second imputation operation to derive supplementary probability information to relating to the low-quality genotypes; using the initial and supplementary probability information relating to the low-quality genotypes to derive a Posterior Genotype Quality (PGQ) value; merging at least some of the observed or the refined variants with the set of imputed variants; and generating a final imputation file.

Figure 19:
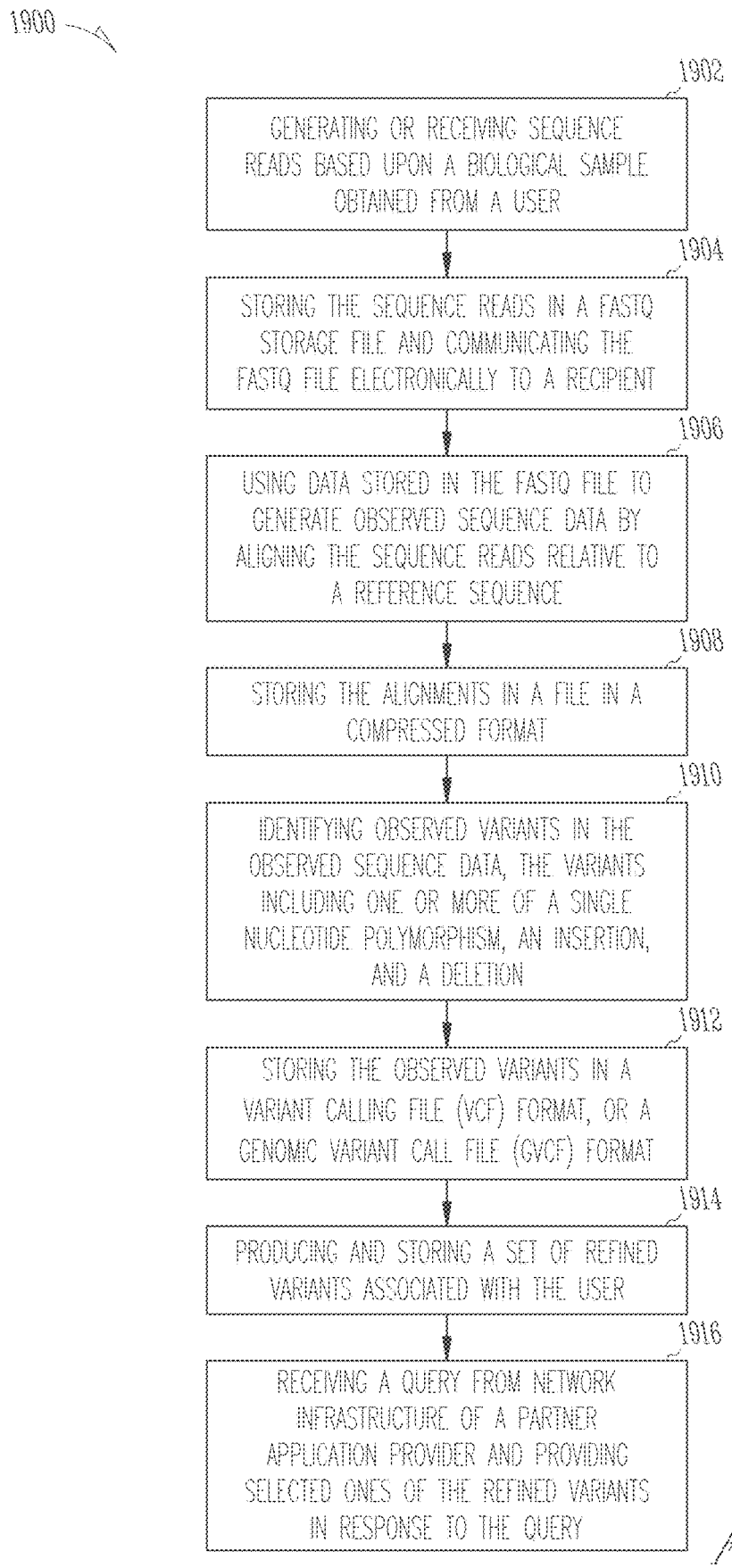

A flow diagram for another example method 1500 is illustrated in FIG. 19. The method 1900 includes: at block 1902, generating or receiving sequence reads based upon a biological sample obtained from a user; at block 1904, storing the sequence reads in a FASTQ storage file and communicating the FASTQ file electronically to a recipient; at block 1906, using data stored in the FASTQ file to generate observed sequence data by aligning the sequence reads relative to a reference sequence; at block 1908, storing the alignments in a file in a compressed format; at block 1910, identifying observed variants in the observed sequence data, the variants including one or more of a single nucleotide polymorphism, an insertion, and a deletion; at block 1912, storing the observed variants in a variant calling file (VCF) format, or a genomic variant call file (GVCF) format; at block 1914, producing and storing a set of refined variants associated with the user; and, at block 1916, receiving a query from network infrastructure of a partner application provider and providing selected ones of the refined variants in response to the query.

The method 1900 may further comprise utilizing a mapping algorithm to compare the sequence of a given read to that of the reference sequence to locate a potentially unique location in the reference sequence that matches the read.

The method 1900 may further comprise storing the alignments in a compressed format in a Binary Alignment Map (BAM) file, and indexing the BAM file relative to the reference sequence to generate a Sequence Alignment Map (SAM) file.

The method 1900 may further comprise processing the BAM (or SAM) file to identify the existence of the observed variants in the observed sequence data.

The method 1900 may further comprising producing at least two variant data files, the at least two variant data files including: a first genomic variant data file (GVCF) providing genomic information about all sites in the sequence reads obtained from the user genome, the sites including both sites with variants and reference call sites without variants; and a second variant data file (VCF) providing genomic information about sites in the sequence reads obtained from the user genome, the genomic information including posterior genotype likelihoods for sites with variants, but not including information about reference call sites without variants.

The method 1900 may further comprise merging the first GVCF and second VCF files to produce a single variant call file, the single variant call file including reference calls from the first GVCF file and variants calls with posterior genotype likelihoods from the second VCF file.

The method 1900 may further comprise using or storing one or more Browser Extensible Data (BED) files defining one or more genomic windows associated with the partner application provider or a partner application, and wherein the selected ones of the refined variants are associated with reference locations within one of the one or more genomic windows.

Figure 20:
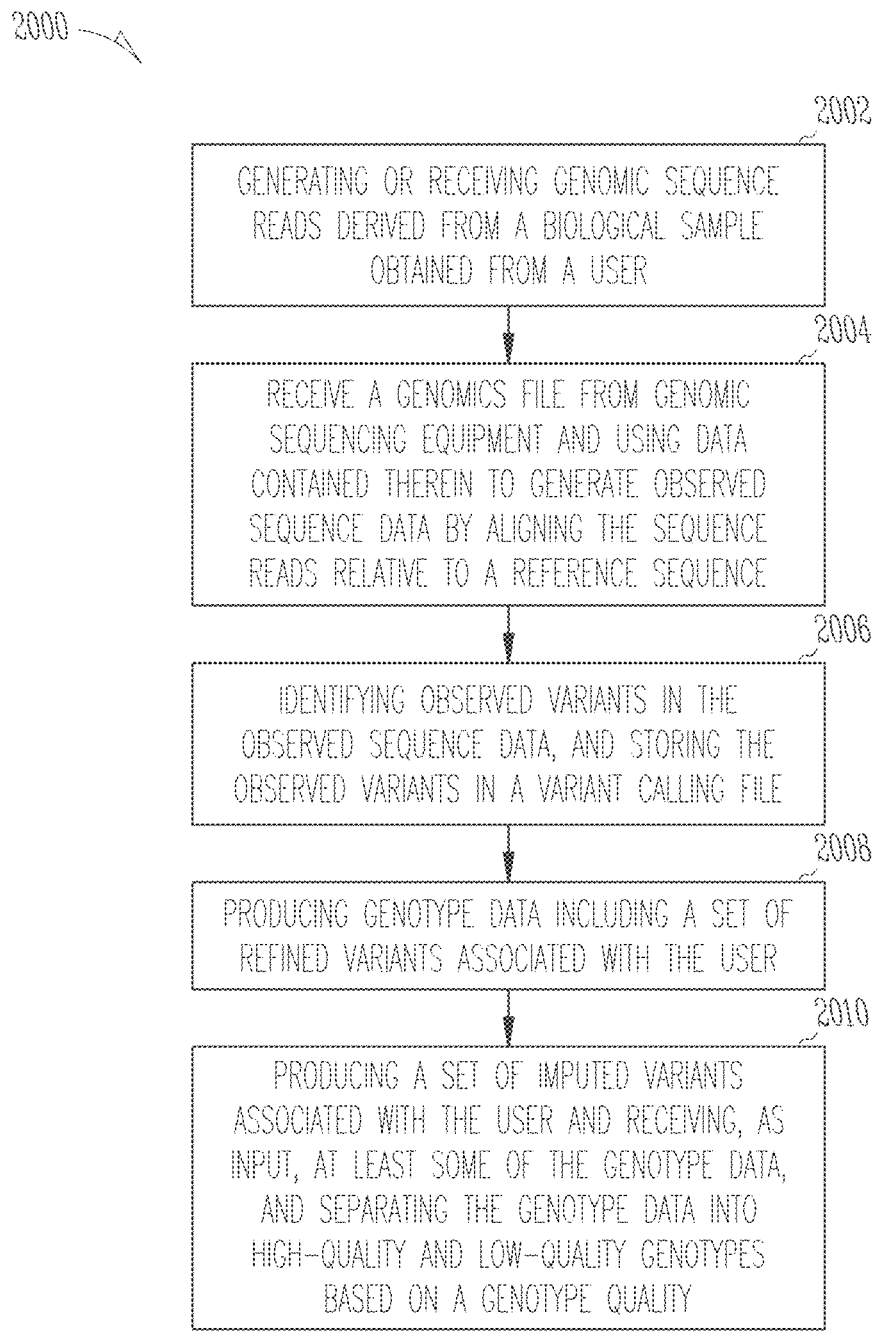

A flow diagram for another example method 2000 is illustrated in FIG. 20. The method 2000 includes: at block 2002, generating or receiving genomic sequence reads derived from a biological sample obtained from a user; at block 2004, receive a genomics file from genomic sequencing equipment and using data contained therein to generate observed sequence data by aligning the sequence reads relative to a reference sequence; at block 2006, identifying observed variants in the observed sequence data, and storing the observed variants in a variant calling file; at block 2008, producing genotype data including a set of refined variants associated with the user; and, at block 2010, producing a set of imputed variants associated with the user and receiving, as input, at least some of the genotype data, and separating the genotype data into high-quality and low-quality genotypes based on a genotype quality.

The method 2000 may further comprise conducting at least a first pre-phasing operation using only the high-quality genotypes to generate phased high-quality haplotypes.

The method 2000 may further comprise conducting at least a first imputation operation using the phased high-quality haplotypes.

The method 2000 may further comprise using an output of the first imputation operation to boost initial probability information relating to the low-quality genotypes to produce boosted genotypes.

The method 2000 may further comprise conducting a second pre-phasing operation using the high-quality genotypes and the boosted genotypes to generate high-quality haplotypes and boosted haplotypes.

The method 2000 may further comprise producing two variant data files, the two variant data files including: a first genomic variant data file (GVCF) providing genomic information about all sites in the sequence reads, the sites including both sites with variants and reference call sites without variants; and a second variant data file (VCF) providing genomic information about sites in the sequence reads, the genomic information including posterior genotype likelihoods for sites with variants, but not including information about reference call sites without variants; conducting a second imputation operation using the high-quality and boosted haplotypes; using an output of the second imputation operation to derive supplementary probability information to relating to the low-quality genotypes; using the initial and supplementary probability information relating to the low-quality genotypes to derive a posterior genotype quality value; merging at least some of the observed or the refined variants with the set of imputed variants; and generating a final imputation file, the final imputation file including at least some of the genetic information stored in the second variant data file (VCF), and at least one posterior genotype quality value.

Figure 21:
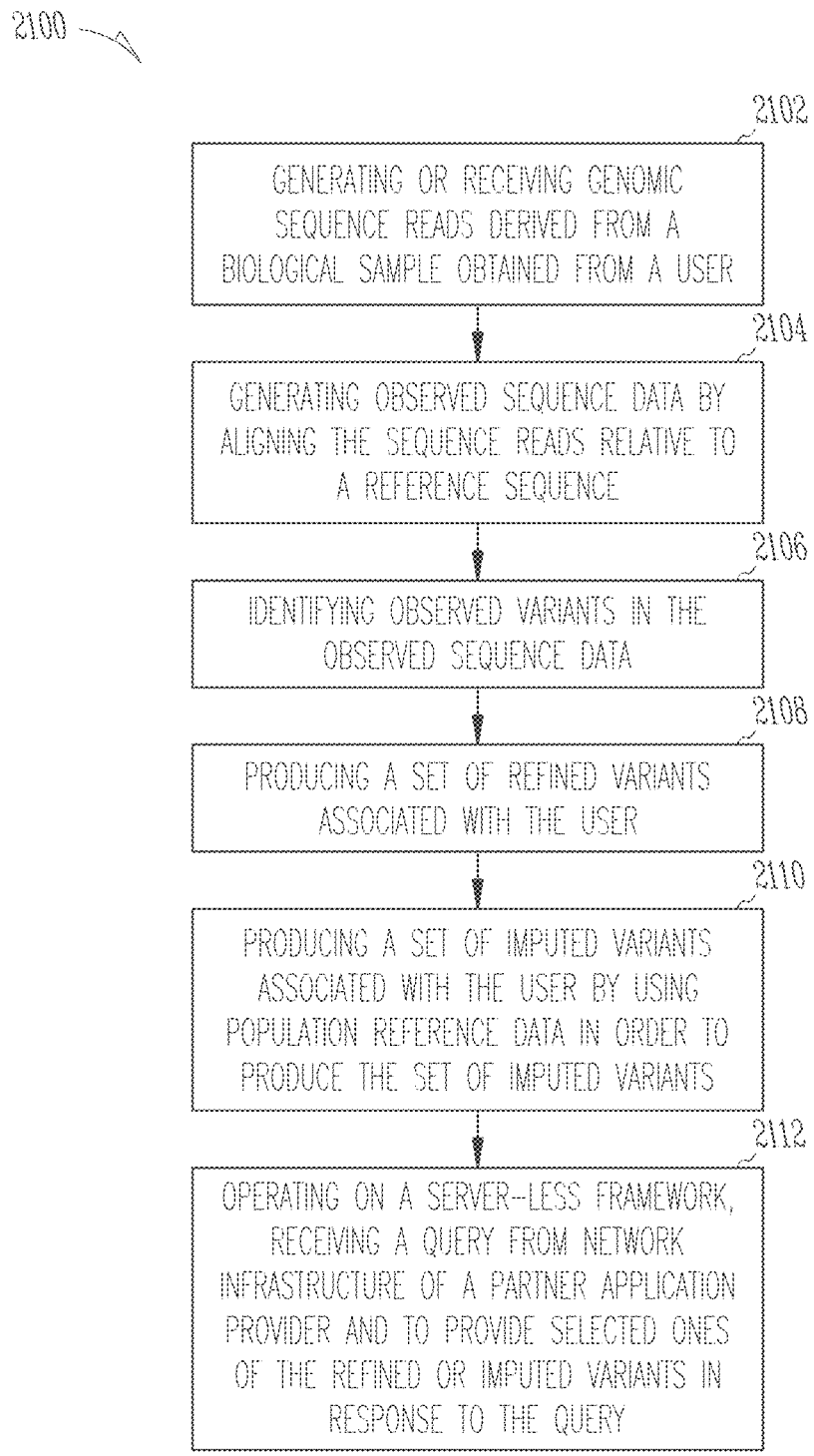

A flow diagram for another example method 2100 is illustrated in FIG. 21. The method 2100 includes: at block 2102, generating or receiving genomic sequence reads derived from a biological sample obtained from a user; at block 2104, generating observed sequence data by aligning the sequence reads relative to a reference sequence; at block 2106, identifying observed variants in the observed sequence data; at block 2108, producing a set of refined variants associated with the user; at block 2110, producing a set of imputed variants associated with the user by using population reference data in order to produce the set of imputed variants; and, at block 2112, operating on a serverless framework, receiving a query from network infrastructure of a partner application provider and to provide selected ones of the refined or imputed variants in response to the query.

The method 2100 may further comprise providing a genomics interface comprising a genomics API endpoint whereby the partner application provider can invoke tasks relating to genomic information comprising at least the selected ones of the refined or imputed variants, and receiving a request to invoke a task relating to the genomic information.

The method 2100 may further comprise receiving, from the partner application provider, via the genomics API endpoint, a user ID identifying a binary tuple of the form (app, customer), or (partner, app), wherein app is a value identifying an application of the partner application provider, partner is a value identifying the partner application provider, and customer is a value identifying the user interacting with the application corresponding to the app.

The method 2100 may further comprise using the user ID supplied by the partner application provider to identify the user within the bioinformatics processing pipeline and perform a look-up of a Browser Extensible Data (BED) file based on the user ID, the (BED) file defining one or more genomic windows associated with the partner application provider or a partner application, and wherein the selected ones of the refined or imputed variants are associated with reference locations within one of the one or more genomic windows.

The method 2100 may further comprise providing, in response to the query, to the partner application provider or partner application, selected ones of the refined or imputed variants asynchronously, and synchronously returning data streams including genomic information to the partner application provider or partner application.

The method 2100 may further comprise providing a partner API endpoint whereby the partner application provider can invoke tasks, based on the user ID, relating to non-genomic information.

Some embodiments include machine-readable media including instructions which, when read by a machine, cause the machine to perform the operations of any one or more of the methodologies summarized above, or described elsewhere herein.

While various embodiments have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above. Although various modules in the different devices are shown to be located in the processors of the device, they can also be located/stored in the memory of the device (e.g., software modules) and can be accessed and executed by the processors. Accordingly, the specification is intended to embrace all such modifications and variations of the disclosed embodiments that fall within the spirit and scope of the appended claims.

The various methods or processes outlined herein may be coded as software that is executable on one or more processors that employ any one of a variety of operating systems or platforms. Additionally, such software may be written using any of a number of suitable programming languages and/or programming or scripting tools, and may be compiled as executable machine language code or intermediate code that is executed on a framework or virtual machine.

In this respect, various inventive concepts may be embodied as a non-transitory computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other non-transitory medium or tangible computer storage medium) encoded with one or more programs that, when executed on one or more computers or other processors, perform methods that implement the various embodiments of the invention discussed above. The non-transitory computer readable medium or media can be transportable, such that the program or programs stored thereon can be loaded onto one or more different computers or other processors to implement various aspects of the present invention as discussed above.

The terms "program" or "software" are used herein in a generic sense to refer to any type of computer code or set of computer-executable instructions that can be employed to program a computer or other processor to implement various aspects of embodiments as discussed above. Additionally, it should be appreciated that according to one aspect, one or more computer programs that when executed perform methods of the present invention need not reside on a single computer or processor, but may be distributed in a modular fashion amongst a number of different computers or processors to implement various aspects of the present invention.

Computer-executable instructions may be in many forms, such as program modules, executed by one or more computers or other devices. Generally, program modules include routines, programs, objects, components, data structures, etc. that perform particular tasks or implement particular abstract data types. Typically, the functionality of the program modules may be combined or distributed as desired in various embodiments.

In addition, data structures may be stored in non-transitory computer-readable media in any suitable form. For simplicity of illustration, data structures may be shown to have fields that are related through location in the data structure. Such relationships may likewise be achieved by assigning storage for the fields with locations in a non-transitory computer-readable medium that convey relationship between the fields. However, any suitable mechanism may be used to establish a relationship between information in fields of a data structure, including through the use of pointers, tags or other mechanisms that establish relationship between data elements.

In addition, various inventive concepts may be embodied as one or more methods, of which an example has been provided. The acts performed as part of the method may be ordered in any suitable way. Accordingly, embodiments may be constructed in which acts are performed in an order different from illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A genomic services system comprising:
a network interface through which are received genomic sequence reads derived from a biological sample obtained from a user; and
one or more processors configured to execute a bioinformatics processing pipeline including:
a read alignment module configured to generate observed sequence data by aligning the sequence reads relative to a reference sequence;
a variant calling module operative to identify observed variants in the observed sequence data;
a variant refinement module configured to produce a set of refined variants associated with the user based on the identified observed variants;
a variant imputation module configured to produce a set of predicted genotypes associated with the user based on population reference genotype data; and
a variant storage module configured to:
receive a first application programming interface (API) call from a network infrastructure of a partner application provider among multiple partner application providers, the received first API call requesting a notification that indicates whether the user consented to share a genomic window that includes selected ones of the refined variants or predicted genotypes with the partner application provider, the genomic window corresponding to the partner application provider;

respond to the received first API call by providing the network infrastructure of the partner application provider with the requested notification, the provided notification indicating that the user consented to share the genomic window that includes the selected ones of the refined variants or predicted genotypes with the partner application provider;

in response to the provided notification that the user consented to share the genomic window that includes the selected ones of the refined variants or predicted genotypes with the partner application provider, receive a second API call from the network infrastructure of the partner application provider, the received second API call requesting genomic information of the user and identifying the genomic window that corresponds to the partner application provider; and based on the provided notification that the user consented to share the genomic window that includes the selected ones of the refined variants or predicted genotypes with the partner application provider, respond to the received second API call by returning the genomic window that corresponds to the partner application provider and includes the selected ones of the refined variants or predicted genotypes to the network infrastructure of the partner application provider identified by the received second API call.

2. The genomic services system of claim 1, wherein the received second API call comprises a unique identifier specifying a user and a partner application, and wherein the selected ones of the refined variants or predicted genotypes correspond to a genomics service being provided by the partner application provider identified by the received second API call.

3. The genomic services system of claim 2, wherein the variant storage module is further configured to use the unique identifier included in the received second API call to perform a look-up of a genomic data file, the genomic data file defining the genomic window that corresponds to the partner application provider.

4. The genomic services system of claim 1, wherein the variant storage module is further configured to store a record of all genomic information of the user provided to the partner application provider.

5. The genomic services system of claim 1, wherein the selected ones of the refined variants or predicted genotypes are returned asynchronously in relation to the request.

6. A method comprising:
receiving genomic sequence reads derived from a biological sample obtained from a user;
generating observed sequence data by aligning the sequence reads relative to a reference sequence;
identifying observed variants in the observed sequence data;
producing a set of refined variants associated with the user based on the identified observed variants;
producing a set of predicted genotypes associated with the user based on population reference genotype data;
receiving a first application programming interface (API) call from a network infrastructure of a partner application provider among multiple partner application providers, the received first API call requesting a notification that indicates whether the user consented to share a genomic window that includes selected ones of the refined variants or predicted genotypes with the partner application provider, the genomic window corresponding to the partner application provider;

responding to the received first API call by providing the network infrastructure of the partner application provider with the requested notification, the provided notification indicating that the user consented to share the genomic window that includes the selected ones of the refined variants or predicted genotypes with the partner application provider;

in response to the provided notification that the user consented to share the genomic window that includes the selected ones of the refined variants or predicted genotypes with the partner application provider, receiving a second API call from the network infrastructure of the partner application provider, the received second API call requesting genomic information of the user and identifying the genomic window that corresponds to the partner application provider; and based on the provided notification that the user consented to share the genomic window that includes the selected ones of the refined variants or predicted genotypes with the partner application provider, responding to the received second API call by returning the genomic window that corresponds to the partner application provider and includes the selected ones of the refined variants or predicted genotypes to the network infrastructure of the partner application provider identified by the received second API call.

7. The method of claim 6, wherein the received second API call comprises a unique identifier specifying a partner application, and wherein the selected ones of the refined variants or predicted genotypes correspond to a genomics service being provided by the partner application provider identified by the received second API call.

8. The method of claim 7, further comprising performing, based on the unique identifier included in the received second API call, a look-up of a genomic data file, the genomic data file defining the genomic window that corresponds to the partner application provider.

9. The method of claim 6, further comprising storing a record of all genomic information of the user provided to the partner application provider.

10. The method of claim 6, wherein the selected ones of the refined variants or predicted genotypes are returned asynchronously in relation to the request.

11. A non-transitory machine-readable medium comprising instructions that, when executed by a machine, cause the machine to perform operations comprising:
receiving genomic sequence reads derived from a biological sample obtained from a user;
generating observed sequence data by aligning the sequence reads relative to a reference sequence;
identifying observed variants in the observed sequence data;
producing a set of refined variants associated with the user based on the identified observed variants;
producing a set of predicted genotypes associated with the user based on population reference genotype data;
receiving a first application programming interface (API) call from a network infrastructure of a partner application provider among multiple partner application providers, the received first API call requesting a notification that indicates whether the user consented to share a genomic window that includes selected ones of the refined variants or predicted genotypes with the partner application provider, the genomic window corresponding to the partner application provider;

responding to the received first API call by providing the network infrastructure of the partner application provider with the requested notification, the provided notification indicating that the user consented to share the genomic window that includes the selected ones of the refined variants or predicted genotypes with the partner application provider;

in response to the provided notification that the user consented to share the genomic window that includes the selected ones of the refined variants or predicted genotypes with the partner application provider, receiving a second API call from the network infrastructure of the partner application provider, the received second API call requesting genomic information of the user and identifying the genomic window that corresponds to the partner application provider; and based on the provided notification that the user consented to share the genomic window that includes the selected ones of the refined variants or predicted genotypes with the partner application provider, responding to the received second API call by returning the genomic window that corresponds to the partner application provider and includes the selected ones of the refined variants or predicted genotypes to the network infrastructure of the partner application provider identified by the received second API call.

12. The non-transitory machine-readable medium of claim 11, wherein the received second API call comprises a unique identifier specifying a user and a partner application, and wherein the selected ones of the refined variants or predicted genotypes correspond to a genomics service being provided by the partner application provider identified by the received second API call.

13. The non-transitory machine-readable medium of claim 12, wherein the operations further comprise performing, based on the unique identifier included in the received second API call, a look-up of a genomic data file, the genomic data file defining the genomic window that corresponds to the partner application provider.

14. The non-transitory machine-readable medium of claim 11, wherein the operations further comprise storing a record of all genomic information of the user provided to the partner application provider.

15. The non-transitory machine-readable medium of claim 11, wherein the selected ones of the refined variants or predicted genotypes are returned asynchronously in relation to the request.

16. The genomic services system of claim 1, wherein:
the variant calling module is further operative to:
output first data including information on all sites in the observed sequence data; and
output second data including posterior genotype likelihoods for variants for each variant in the observed sequence data; and
the variant imputation module is further configured to merge the first data with the second data to produce the set of refined variants.

17. The genomic services system of claim 1, wherein the variant imputation module is configured to:
impute variants based on phased high-quality haplotypes;
boost probability information relating to low-quality genotypes to produce boosted genotypes; and
combine the high-quality haplotypes and the boosted genotypes to create the set of predicted genotypes.

18. The genomic services system of claim 1, wherein the set of predicted genotypes are not directly assayed in the biological sample obtained from the user.

19. The genomic services system of claim 3, wherein genomic information within the genomic window that corresponds to the partner application provider is accessible by the partner application provider or the partner application, and wherein genomic information outside of the genomic window that corresponds to the partner application provider is inaccessible by the partner application provider and the partner application.

20. The genomic services system of claim 2, wherein the unique identifier preserves anonymity of the user in relation to the partner application provider.

* * * * *

UNITED STATES PATENT AND TRADEMARK OFFICE
CERTIFICATE OF CORRECTION

PATENT NO. : 10,622,095 B2
APPLICATION NO. : 15/872655
DATED : April 14, 2020
INVENTOR(S) : Lu et al.

Page 1 of 1

It is certified that error appears in the above-identified patent and that said Letters Patent is hereby corrected as shown below:

On the Title Page

Item (57), in "Abstract", in Column 2, Line 5, after "user", insert --.--

In the Specification

In Column 3, Line 19, delete "embodiment." and insert --embodiment (SEQ ID NO: 1).-- therefor In Column 31, Line 22, delete "1500" and insert --1900-- therefor Signed and Sealed this
Seventh Day of July, 2020

Andrei Iancu
*Director of the United States Patent and Trademark Office*

SEQUENCE LISTING

```
<160> NUMBER OF SEQ ID NOS: 1

<210> SEQ ID NO 1
<211> LENGTH: 18
<212> TYPE: DNA
<213> ORGANISM: Artificial Sequence
<220> FEATURE:
<223> OTHER INFORMATION: A synthetic oligonucleotide sequence

<400> SEQUENCE: 1
attcgtacta acgttggc                                                 18
```